US012811014B2

(12) United States Patent
Keshavjee et al.

(10) Patent No.: US 12,811,014 B2
(45) Date of Patent: Nov. 24, 2026

(54) ASSESSMENT OF EX VIVO DONOR LUNGS USING LUNG RADIOGRAPHS

(71) Applicant: University Health Network, Toronto (CA)

(72) Inventors: Shafique Keshavjee, Toronto (CA); Bo Wang, Toronto (CA); Marcelo Cypel, Toronto (CA); Andrew Sage, Toronto (CA); Micheal Chad McInnis, Toronto (CA)

(73) Assignee: University Health Network, Toronto (CA)

( * ) Notice: Subject to any disclaimer, the term of this patent is extended or adjusted under 35 U.S.C. 154(b) by 52 days.

(21) Appl. No.: 18/842,361

(22) PCT Filed: Feb. 28, 2023

(86) PCT No.: PCT/CA2023/050259
§ 371 (c)(1),
(2) Date: Aug. 28, 2024

(87) PCT Pub. No.: WO2023/159331
PCT Pub. Date: Aug. 31, 2023

(65) Prior Publication Data

US 2025/0182903 A1 Jun. 5, 2025

Related U.S. Application Data

(60) Provisional application No. 63/314,930, filed on Feb. 28, 2022.

(51) Int. Cl.
*G16H 50/30* (2018.01)

(52) U.S. Cl.
CPC .................................. *G16H 50/30* (2018.01)

(58) Field of Classification Search
CPC ........ G16H 50/30; G16H 20/40; G16H 30/40; G16H 50/20; G16H 50/70; G06N 3/0464; G06N 5/01; G06N 20/00
See application file for complete search history.

(56) References Cited

U.S. PATENT DOCUMENTS 6,939,668 B2 9/2005 Keshavje
9,835,630 B2 12/2017 Keshavjee
(Continued)

FOREIGN PATENT DOCUMENTS

WO 2006135781 A2 12/2006
WO 2014127463 A1 8/2014
(Continued)

OTHER PUBLICATIONS

Jacob et al., "Transplantation of a three-lobed donor left lung: A case report," SAGE Open Medical Case Reports, vol. 7, pp. 1-3. (Year: 2019).*
(Continued)

*Primary Examiner* — Kiho Kim
(74) *Attorney, Agent, or Firm* — Morrison & Foerster LLP

(57) ABSTRACT

Methods, devices, and systems for predicting transplant suitability of an ex vivo donor lung and/or patient outcome following transplant of the donor lung are described. For example, the method comprises: measuring in a radiograph of the donor lung at least two radiographic features in a plurality of lobes; determining in each of the lobes of the plurality of lobes a lobar score for each of the radiographic features measured; combining the lobar score of each of the lobes of the plurality of lobes to generate a radiograph lung score for each of the radiographic features measured; comparing the radiograph lung score with a control radiograph lung score or a cut-off level for a corresponding radiographic feature; and predicting the transplant suitability of the donor
(Continued)

lung and/or patient outcome following transplant of the donor lung based on the comparison of the radiograph lung score with the control radiograph lung score or cut-off level.

24 Claims, 8 Drawing Sheets

(56) References Cited

U.S. PATENT DOCUMENTS

| | | | |
|---|---|---|---|
| 10,000,809 | B2 | 6/2018 | Keshavjee |
| 2012/0330438 | A1 | 12/2012 | Keshavjee |
| 2015/0377904 | A1 | 12/2015 | Keshavjee |
| 2017/0030909 | A1 | 2/2017 | Oved |
| 2019/0244356 | A1 | 8/2019 | Ayyat |
| 2020/0138015 | A1 | 5/2020 | Bagnato |
| 2020/0241004 | A1 | 7/2020 | Keshavjee |
| 2020/0253195 | A1 | 8/2020 | Bagnato |
| 2021/0338387 | A1 | 11/2021 | Inam |
| 2022/0341944 | A1 | 10/2022 | Keshavjee |
| 2025/0182902 | A1 | 6/2025 | Keshavjee et al. |

FOREIGN PATENT DOCUMENTS

| | | |
|---|---|---|
| WO | 2016094330 | 6/2016 |
| WO | 2017063074 A1 | 4/2017 |
| WO | 2020118452 A1 | 6/2020 |

OTHER PUBLICATIONS

Chambers et al., The International Thoracic Organ Transplant Registry of the International Society for Heart and Lung Transplantation: Thirty-eighth adult heart transplantation report—2021; Focus on recipient characteristics. J Heart Lung Transplant. 2021 (13 pages).
Valapour et al., OPTN/SRTR 2018 Annual Data Report: Lung. Am J Transplant. 2020; 20 Suppl s1: 427-508 (82 pages).
Sadaria et al., "Cytokine Expression Profile in Human Lungs Undergoing Normothermic Ex-Vivo Lung Perfusion", Ann Thorac Surg, (20110000), vol. 92, doi:10.1016/j.athoracsur.2011.04.027, pp. 478-484 (7 pages).
Cypel and Keshavjee, Extracorporeal lung perfusion (ex-vivo lung perfusion): Current Opinion in Organ Transplantation. 2016;21(3):329-335. doi:10.1097/MOT.0000000000000320 (7 pages).
Yeung et al., Ex-vivo lung perfusion: the model for the organ reconditioning hub. Current Opinion in Organ Transplantation. 2017;22(3):287-289. doi:10.1097/MOT.0000000000000404 (3 pages).
Weathington et al., Ex vivo lung perfusion as a human platform for preclinical small molecule testing. JCI Insight. 2018;3(19):e95515. doi:10.1172/jci.insight.95515 (12 pages).
Cypel et al., Normothermic ex vivo lung perfusion: Does the indication impact organ utilization and patient outcomes after transplantation? The Journal of Thoracic and Cardiovascular Surgery. 2020;159(1):346-355.e1. doi:10.1016/j.jtcvs.2019.06.123 (11 pages).
Cypel, M. et al. Technique for prolonged normothermic ex vivo lung perfusion. J Heart Lung Transplant 27, 1319-1325 (2008) (7 pages).
Murala et al., Ex vivo lung perfusion: how we do it. Indian J Thorac Cardiovasc Surg. 2021: 1-12 (12 pages).
Sage et al., Prediction of donor related lung injury in clinical lung transplantation using a validated ex vivo lung perfusion inflammation score. The Journal of Heart and Lung Transplantation. Published online Mar. 2021: S1053249821022191. doi:10.1016/j.healun.2021.03.002 (9 pages).
Yeung et al. Outcomes after transplantation of lungs preserved for more than 12 h: a retrospective study. The Lancet Respiratory Medicine. 2017;5(2):119-124. doi:10.1016/S2213-2600(16)30323-X (6 pages).
Machuca et al., Lung Transplantation With Donation After Circulatory Determination of Death Donors and the Impact of Ex Vivo Lung Perfusion: DCDD Lung Transplantation and EVLP. American Journal of Transplantation. 2015;15(4):993-1002. doi:10.1111/ajt.13124 (10 pages).
Hansell et al., Fleischner Society: glossary of terms for thoracic imaging. Radiology. 2008; 246: 697-722 (26 pages).
Tian et al., Outcomes of marginal donors for lung transplantation after ex vivo lung perfusion: A systematic review and meta-analysis. The Journal of Thoracic and Cardiovascular Surgery. 2020;159(2):720-730.e6. doi:10.1016/j.jtcvs.2019.07.087 (17 pages).
Egan et al., Ex Vivo Evaluation of Human Lungs for Transplant Suitability. The Annals of Thoracic Surgery. 2006;81(4):1205-1213. doi:10.1016/j.athoracsur.2005.09.034 (9 pages).
Fisher et al., An observational study of Donor Ex Vivo Lung Perfusion in UK lung transplantation: Develop-UK. Health Technol Assess. 2016;20(85):1-276. doi: 10.3310/hta20850 (310 pages).
Wallinder et al., Transplantation of initially rejected donor lungs after ex vivo lung perfusion. The Journal of Thoracic and Cardiovascular Surgery. 2012; 144(5):1222-1228. doi:10.1016/j.jtcvs.2012.08.011 (7 pages).
International Search Report and Written Opinion mailed May 17, 2023 in International Patent Application No. PCT/CA2023/050259 (16 pages).
Martens, A. et al., Steroids can Reduce Warm Ischemic Reperfusion Injury in a Porcine Donation after Circulatory Death Model with Ex Vivo Lung Perfusion Evaluation, Transplant International, 2016, 29, 1237-1246 (10 pages).
Andreasson, A. S. et al., Profiling inflammation and tissue injury markers in perfusate and bronchoalveolar lavage fluid during human ex vivo lung perfusion. Eur J Cardiothorac Surg. 2017;51(3):577-86 (10 pages).
Nakajima, D. et al. Lung Lavage and Surfactant Replacement During Ex Vivo Lung Perfusion for Treatment of Gastric Acid Aspiration-Induced Donor Lung Injury, J Heart Lung Transplant, 2017, 36, 577-585 (9 pages).
Ayyat, K. S. et al. Reperfusion Inflammatory State of Human Lungs during Cellular Ex-Vivo Perfusion, J Heart Lung 10 Transplant, Apr. 2019, 38(4), p. S241 (1 page).
Andreasson, A. S. et al. The role of interleukin-1beta as a predictive biomarker and potential therapeutic target during clinical ex vivo lung perfusion. J Heart Lung Transplant. 2017; 36(9):985-95 (11 pages).
Cypel, M. Ex Vivo Lung Perfusion (EVLP), Curr Respir Care Rep, 2013, 2, 167-172 (6 pages).
Lin Huiqing et al., [alpha]1-Anti-trypsin improves function of porcine donor lungs during ex-vivo lung perfusion. Journal of Heart and Lung Transplantation. Elsevier, Amsterdam, NL. vol. 37, No. 4, Oct. 2, 2017, pp. 656-666 (11 pages).
Machuca, T. N. et al., Protein expression profiling predicts graft performance in clinical ex vivo lung perfusion. Ann Surg 261, 591-597 (2015) (8 pages).
Jain et al., Basic science of acute lung injury. Surgery, Medicine Publishing, Abington. Elsevier Imprint, GB. vol. 25, No. 3, Apr. 21, 2007, pp. 112-116 (5 pages).
Determann Rogier M. et al., Serial changes in soluble triggering receptor expressed on myeloid cells in the lung during development of ventilator-associated pneumonia. Intensive Care Medicine, Springer Berlin Heidelberg, Berlin/Heidelberg. vol. 31, No. 11, Sep. 30, 2005, pp. 1495-1500 (6 pages).
Shahzad et al., "Standard Operating Procedures in Clinical Gene Expression Biomarker Panel Development", Batch Effects and Noise in Microarray Experiments, Chichester, UK, John Wiley & Sons, Ltd, (Oct. 30, 2009), pp. 203-213, doi:10.1002/9780470685983.ch17, ISBN 978-0-470-74138-2, XP055966521 (11 pages).
Zhang and Drabier., "Chapter 9. Bioinformatics and Statistics: Computational Discovery, Verification, and Validation of Functional Biomarkers:", Peptide-based Drug Discovery : Challenges and New Therapeutics, GB, Royal Society of Chemistry, Cambridge, (Jan. 1, 2013), pp. 243-268, doi:10.1039/9781849734363-00243, ISSN 2041-3211, ISBN 978-1-78262-732-6, XP055966537 (1 page).
Boffini, M., et al. High Levels of Cytokines in the Perfusate During Ex-Vivo Lung Perfusion Correlates with 23 Persistence of Poor

(56) References Cited

OTHER PUBLICATIONS

Graft Function After Lung Transplantation Using Reconditioned Grafts. The Journal of Heart and Lung Transplantation, vol. 36, No. 4S, Apr. 2017, p. S74 (1 page).
Cypel, M. et al. The clinical potential of ex vivo lung perfusion. Expert Rev Respir Med 6, 27-35 (2012) (10 pages).
Kaneda et al. Pre-Implantation Multiple Cytokine mRNA Expression Analysis of Donor Lung Grafts Prdicts Survival After Lung Transplantation in Humans. American Journal of Transplantation, 2006, vol. 6, issue 3, pp. 544-551 (8 pages).
Machuca, T. N. et al., "The Role of the Endothelin-1 Pathway as a Biomarker for Donor Lung Assessment in Clinical Ex Vivo Lung Perfusion" Journal of Heart and Lung Transplantation, vol. 34, No. 6, Jun. 2015, pp. 849-857 (9 pages).
Okamoto, T. et al. "Ex Vivo Lung Perfusion of Rejected Human Donor Lungs; Are Donor Lungs with Prolonged Cold 17 Ischemic Time Re-Conditioned by EVLP?" Journal of Heart and Lung Transplantation, vol. 32, No. 4, Apr. 1, 2013, pp. S67 (1 page).
Parsons, P. E., et al. Elevated plasma levels of soluble TNF receptors are associated with morbidity and mortality in patients with acute lung injury. AJP—Lung Cell Mol Physiol. vol. 288, Mar. 2005 pp. L426-L431 (6 pages).
Porfyridis, Ilias et al. Diagnostic value of triggering receptor expressed on myeloid cells-1 and C-reactive protein for patients with lung infiltrates: an observational study. BMC Infectious Diseases, 2010, 10:286 (10 pages).
Porteous, M. K. et al. Clinical risk factors and prognostic model for primary graft dysfunction after lung transplantation in patients with pulmonary hypertension. AnnalsATS, vol. 14, 10, 1514-1522 (2017) (9 pages).
Saito et al. Impact of Cytokine Expression in the Pre-Implanted Donor Lung on the Development of Chronic Lung Allograf Dysfunction Subtypes. American Journal of Transplantation, 2013, vol. 13, issue 12, pp. 3192-3201 (10 pages).
Salama, M, et al. "Concomitant Endothelin-1 Overexpression in Lung Transplant Donors and Recipients Predicts Primary Graft Dysfunction", American Journal of Transplantation, vol. 10, No. 3, Mar. 1, 2009, pp. 628-636 (9 pages).
Salama, M. et al. "Endothelin-1 is a useful biomarker for early detection of bronchiolitis obliterans in lung transplant recipients", Journal of Thoracic and Cardiovascular Surgery, vol. 140, No. 6, Dec. 1, 2010, pp. 1422-1427 (6 pages).
Ceresa et al., Machine perfusion of the liver: applications in transplantation and beyond. Nat Rev Gastroenterol Hepatol. Jan. 7, 2022. doi: 10.1038/s41575-021-00557-8. Epub ahead of print (11 pages).
Ardehali et al., Ex-vivo perfusion of donor hearts for human heart transplantation (Proceed II): a prospective, open-label, multicentre, randomised non-inferiority trial. Lancet. Jun. 27, 2015;385(9987):2577-84. doi: 10.1016/S0140-6736(15)60261-6. Epub Apr. 14, 2015. PMID: 25888086 (8 pages).
Kaths et al., Normothermic Ex Vivo Kidney Perfusion for the Preservation of Kidney Grafts prior to Transplantation. J Vis Exp. Jul. 15, 2015;(101):e52909. doi: 10.3791/52909. PMID: 26275014; PMCID: PMC4544894 (14 pages).
Prudhomme et al., Ischemia-Reperfusion Injuries Assessment during Pancreas Preservation. Int J Mol Sci. May 13, 2021;22(10):5172. doi: 10.3390/ijms22105172. PMID: 34068301; PMCID: PMC8153272 (16 pages).
Whitson and Black, Organ assessment and repair centers: The future of transplantation is near. World J Transplant. Jun. 24, 2014;4(2):40-2. doi: 10.5500/wjt.v4.i2.40. PMID: 25032094; PMCID: PMC4094951 (4 pages).
Keshavjee, Human organ repair centers: Fact or fiction?. JTCVS. Sep. 1, 2020;3:164-168 (5 pages).
Suarez-Pierre et al., Measuring the effect of the COVID-19 pandemic on solid organ transplantation. Am J Surg. Dec. 30, 2021:S0002-9610(21)00784-4. doi: 10.1016/j.amjsurg.2021.12.036. Epub ahead of print. PMID: 34980465; PMCID: PMC8717917 (6 pages).
Watanabe et al., Ex vivo lung perfusion. J Thorac Dis. Nov. 2021;13(11):6602-6617. doi: 10.21037/jtd-2021-23. PMID: 34992839; PMCID: PMC8662477 (16 pages).
Okahara et al., Common Criteria for Ex Vivo Lung Perfusion Have No Significant Impact on Posttransplant Outcomes. Ann Thorac Surg. Apr. 2021;111(4):1156-1163. doi: 10.1016/j.athoracsur.2020.06.081. Epub Sep. 2, 2020. PMID: 32890490 (8 pages).
Di Nardo et al., Predicting donor lung acceptance for transplant during ex vivo lung perfusion: The EX vivo lung Perfusion pREdiction (Expire). Am J Transplant. Nov. 2021;21(11):3704-3713. doi: 10.1111/ajt.16616. Epub Jun. 11, 2021. PMID: 33872459 (10 pages).
Ferdinand et al., Transcriptional analysis identifies potential novel biomarkers associated with successful ex-vivo perfusion of human donor lungs. Clin Transplant. Dec. 26, 2021:e14570. doi: 10.1111/ctr.14570. Epub ahead of print. PMID: 34954872 (11 pages).
Machuca et al., The role of the endothelin-1 pathway as a biomarker for donor lung assessment in clinical ex vivo lung perfusion. J Heart Lung Transplant. Jun. 2015;34(6):849-57. doi: 10.1016/j.healun.2015.01.003. Epub Jan. 16, 2015. PMID: 25907141 (10 pages).
Hashimoto et al., Soluble Adhesion Molecules During Ex Vivo Lung Perfusion Are Associated With Posttransplant Primary Graft Dysfunction. Am J Transplant. May 2017;17(5):1396-1404. doi: 10.1111/ajt.14160. Epub Feb. 1, 2017. PMID: 27977885 (9 pages).
Hashimoto et al., Higher M30 and high mobility group box 1 protein levels in ex vivo lung perfusate are associated with primary graft dysfunction after human lung transplantation. J Heart Lung Transplant. Jun. 21, 2017:S1053-2498(17)31870-3. doi: 10.1016/j.healun.2017.06.005. Epub ahead of print. PMID: 28689646 (10 pages).
Caldarone et al., Neutrophil extracellular traps in ex vivo lung perfusion perfusate predict the clinical outcome of lung transplant recipients. Eur Respir J. Apr. 4, 2019;53(4):1801736. doi: 10.1183/13993003.01736-2018. PMID: 30655281 (5 pages).
Lee et al., Critical care management of the lung transplant recipient. Curr Respir Care Rep. 2012;1(3):168-176. doi: 10.1007/s13665-012-0018-9. Epub Jun. 22, 2012. PMID: 32288970; PMCID: PMC7102351 (9 pages).
Clausen and Cantu, Primary graft dysfunction: what we know. J Thorac Dis. Nov. 2021;13(11):6618-6627. doi: 10.21037/jtd-2021-18. PMID: 34992840; PMCID: PMC8662499 (10 pages).
Abrams et al., Risks and Benefits of Ultra-Lung-Protective Invasive Mechanical Ventilation Strategies with a Focus on Extracorporeal Support. Am J Respir Crit Care Med. Jan. 19, 2022. doi: 10.1164/rccm.202110-2252CP. Epub ahead of print. PMID: 35044901 (10 pages).
Bellini et al., Artificial intelligence in thoracic surgery: a narrative review. J Thorac Dis. Dec. 2021;13(12):6963-6975. doi: 10.21037/jtd-21-761. PMID: 35070380; PMCID:PMC8743413 (13 pages).
Cypel et al., Technique for Prolonged Normothermic Ex Vivo Lung Perfusion. The Journal of Heart and Lung Transplantation. 2008;27(12):1319-1325 doi:10.1016/j.healun.2008.09.003 (8 pages).
Boffini et al., Ex Vivo Lung Perfusion Increases the Pool of Lung Grafts: Analysis of Its Potential and Real Impact on a Lung Transplant Program. Transplantation Proceedings. 2013;45(7):2624-2626. doi:10.1016/j.transproceed.2013.08.004 (3 pages).
Hsin et al., Metabolic Profile of Ex Vivo Lung Perfusate Yields Biomarkers for Lung Transplant Outcomes. Annals of Surgery. 2018;267(1):196-197. doi:10.1097/SLA.0000000000002016 (2 pages).
Leligdowicz et al., The endogenous capacity to produce proinflammatory mediators by the ex vivo human perfused lung. ICMx. 2020;8(1):56. doi:10.1186/s40635-020-00343-x (15 pages).
Kanou et al., Cell-free DNA in human ex vivo lung perfusate as a potential biomarker to predict the risk of primary graft dysfunction in lung transplantation. J Thorac Cardiovasc Surg. Aug. 2021;162(2):490-499.e2. doi: 10.1016/j.jtcvs.2020.08.008. Epub Aug. 11, 2020. PMID: 32928548 (12 pages).
Shin et al., Use of metabolomics to identify strategies to improve and prolong ex vivo lung perfusion for lung transplants. The Journal of Heart and Lung Transplantation. 2021;40(6):525-535. doi:10.1016/j.healun.2021.02.002 (11 pages).
Rosler and Herold, Lung epithelial GM-CSF improves host defense function and epithelial repair in influenza virus pneumonia—a new therapeutic strategy? Mol Cell Pediatr. 2016;3(1):29. doi:10.1186/s40348-016-0055-5 (6 pages).

(56) References Cited

OTHER PUBLICATIONS

Michlewska et al., Macrophage phagocytosis of apoptotic neutrophils is critically regulated by the opposing actions of pro-inflammatory and anti-inflammatory agents: key role for TNF-α. FASEB j. 2009;23(3):844-854. doi:10.1096/fj.08-121228 (11 pages).
Lecube et al., TNF-α system and lung function impairment in obesity. Cytokine. 2011;54(2):121-124. doi:10.1016/j.cyto.2011.01.010 (4 pages).
Baciu et al., Transcriptomic investigation reveals donor specific gene signatures in human lung transplants. Eur Respir J. Published online Jan. 1, 2020:2000327. doi:10.1183/13993003.00327-2020 (12 pages).
Shi et al., Diagnostic Value of sTREM-1 in Bronchoalveolar Lavage Fluid in ICU Patients With Bacterial Lung Infections: A Bivariate Meta-Analysis. Rojas M, ed. PLoS ONE. 2013;8(5):e65436. doi:10.1371/journal.pone.0065436 (9 pages).
Wright et al., sTREM-1 predicts mortality in hospitalized patients with infection in a tropical, middle-income country. BMC Med. 2020;18(1):159. doi:10.1186/s12916-020-01627-5 (9 pages).
Mason and Graham, Areas beneath the relative operating characteristics (ROC) and relative operating levels (ROL) curves: Statistical significance and interpretation. Q J R Meteorol Soc. 2002;128(584):2145-2166. doi:10.1256/003590002320603584 (22 pages).
International Search Report and Written Opinion mailed May 11, 2023 in International Patent Application No. PCT/CA2023/050251 (22 pages).
Kamaleswaran et al., Artificial intelligence may predict early sepsis after liver transplantation. Frontiers in Physiology, 2021, vol. 12, p. 692667 (9 pages).
Kawakita et al., Personalized prediction of delayed graft function for recipients of deceased donor kidney transplants with machine learning. Scientific Reports, 2020, vol. 10, No. 1, p. 18409 (13 pages).
Zarkowsky and Stonko, Artificial intelligence's role in vascular surgery decision-making. In: Seminars in Vascular Surgery. WB Saunders, 2021. p. 260-267 (3 pages).
Gotlieb et al., The promise of machine learning applications in solid organ transplantation. NPJ digital medicine, 2022, vol. 5, No. 1, p. 89 (13 pages).
Sage et al., InsighTx: A Machine-Learning Model That Accurately Predicts Transplant Outcomes During Ex Vivo Lung Perfusion. The Journal of Heart and Lung Transplantation, Apr. 2022, vol. 41, No. 4, p. S15 (1 page).
Zhou et al., Kinetic Modeling of Ex Vivo Lung Perfusion Biomarkers for the Prediction of Lung Transplant Outcomes. The Journal of Heart and Lung Transplantation, 2022, vol. 41, No. 4, p. S256 (1 page).
Cypel, M. et al. Normothermic ex vivo lung perfusion in clinical lung transplantation. N Engli J Med 364, 1431-1440 (2011) (10 pages).
Cypel, M. et al. Normothermic ex vivo perfusion prevents lung injury compared to extended cold preservation for transplantation. Am J Transplant 9, 2262-2269 (2009) (8 pages).
Cypel, M. et al. Novel approaches to expanding the lung donor pool: donation after cardiac death and ex vivo conditioning. Clin Chest Med 32, 233-244 (2011) (12 pages).
Hsin, M. K. et al. Extension of donor lung preservation with hypothermic storage after normothermic ex vivo lung perfusion. J Heart Lung Transplant 35, 130-136 (2016) (7 pages).
Machuca, T. N. et al. Lung transplantation with donation after circulatory determination of death donors and the impact of ex vivo lung perfusion. Am J Transplant 15, 993-1002 (2015) (10 pages).
Cypel et al., Technique for prolonged normothermic ex vivo lung perfusion. J Heart Lung Transplant. Dec. 2008;27(12):1319-25. doi: 10.1016/j.healun.2008.09.003. PMID: 19059112 (8 pages).
Divithotawela et al., Long-term Outcomes of Lung Transplant With Ex Vivo Lung Perfusion. JAMA Surg. Dec. 1, 2019;154(12):1143-1150. doi: 10.1001/jamasurg.2019.4079. PMID: 31596484; PMCID: PMC6802423 (18 pages).
Possoz et al., Ex vivo lung perfusion prior to transplantation: an overview of current clinical practice worldwide. J Thorac Dis. Apr. 2019;11(4):1635-1650. doi: 10.21037/jtd.2019.04.33. PMID: 31179109; PMCID: PMC6531747 (16 pages).
Chen and Guestrin, Xgboost: A scalable tree boosting system. Proceedings of the 22nd ACM SIGKDD International Conference on Knowledge Discovery and Data Mining, 2016:785-794 (10 pages).
Cypel et al., Experience with the first 50 ex vivo lung perfusions in clinical transplantation. The Journal of Thoracic and Cardiovascular Surgery. 2012;144(5):1200-1207. doi:10.1016/j.jtcvs.2012.08.009 (8 pages).
Yeung et al., Physiologic assessment of the ex vivo donor lung for transplantation. J Heart Lung Transplant. Oct. 2012;31(10):1120-1126 (7 pages).
Chao et al. (Apr. 2022). "Standardized Radiographic Evaluation of Human Donor Lungs During Ex Vivo Lung Perfusion Predicts Lung Injury and Lung Transplant Outcomes," The Journal of Heart and Lung Transplantation 41(4) Supplement: S13-S14.
Extended European Search Report dated Apr. 2, 2026, directed to EP Application No. 23758871.0; 11 pages.
Extended European Search Report dated Jan. 29, 2026, directed to EP Application No. 23758869.4; 10 pages.
Marklin et al. (Feb. 2021). "Ventilation in the prone position improves oxygenation and results in more lungs being transplanted from organ donors with hypoxemia and atelectasis," The Journal of Heart and Lung Transplantation 40(2): 120-127.
Ware et al. (Feb. 2012). "Comparison of chest radiograph scoring to lung weight as a quantitative index of pulmonary edema in organ donors," Clinical Transplantation 26(5): 665-671.

* cited by examiner

ASSESSMENT OF EX VIVO DONOR LUNGS USING LUNG RADIOGRAPHS

CROSS-REFERENCE TO RELATED PATENT APPLICATION

This application is a national phase entry of PCT/CA2023/050259 filed Feb. 28, 2023 (which designates the U.S.), which claims priority from U.S. Provisional Patent Application No. 63/314,930 filed Feb. 28, 2022; the entire contents of each of which hereby incorporated herein by reference in their entirety.

FIELD

The present disclosure relates to methods, devices and/or systems of predicting transplant suitability and/or post-transplant outcomes of ex vivo donor lung grafts by assessing lung radiographs, and more particularly to methods, devices and/or systems of predicting transplant suitability and/or post-transplant outcomes of ex vivo donor lung grafts undergoing ex vivo lung perfusion (EVLP) by assessing lung radiographs and/or applying machine learning to at least two radiographic features.

BACKGROUND

Lung transplantation is an increasingly used procedure in patients with end stage lung disease.[1] The International Society for Heart and Lung Transplantation report almost 70,000 lung transplant procedures having been performed to date yet there continues to be demand for lung transplantation and wait lists grow.[1,2] A major component of this donor lung shortage is that most donor lungs are, in practice, deemed not suitable for lung transplantation because of perceived lung injury.[3-5]

Ex vivo lung perfusion (EVLP) sustains donor lungs prior to transplantation and allows the surgical team to better assess if the lungs are suitable for transplantation.[3,6] The EVLP platform has significantly augmented donor lung evaluation and repair.[4,6-8] In this procedure, the donor lung is attached to a normothermic EVLP circuit where the lungs are ventilated and perfused.[5,9,10] Monitoring of the donor lung on EVLP includes physiological assessments, as well as biochemical and molecular measurements.[4,7,11] Evaluation of the donor lung, patient outcomes, and survival analyses have shown that outcomes for donor lungs on EVLP are not significantly different from conventional transplantation.[12-14]

Although radiographs of donor lungs are used, features or findings appearing on the radiographs are not systematically assessed for decision-making. There is a need for methods, devices and/or systems that can improve decision making pertaining to the use of donor lungs.

SUMMARY

In one aspect, the inventors have identified several radiographic features that can be used to improve decision making, for example radiographic features that are differentially detected in EVLP treated donor lungs, that are associated with donor lung suitability for transplant and with one or more patient outcomes following transplant.

In another aspect, the inventors have identified a scoring method that may improve the predictive power of the radiographic features described herein.

The disclosure provides in an aspect, methods for predicting transplant suitability and patient outcome (PO) risk.

An aspect of the present disclosure is a method for predicting transplant suitability of an ex vivo donor lung, optionally an ex vivo donor lung undergoing ex vivo lung perfusion (EVLP) and/or patient outcome following transplant of the donor lung, comprising:

measuring in a radiograph of the donor lung at least two radiographic features in a plurality of lobes of the donor lung, the radiographic features optionally selected from consolidation, infiltrate, atelectasis, nodule and interstitial line, and the plurality of lobes selected from right upper lobe, right middle lobe, right lower lobe, left upper lobe, lingula and left lower lobe;

determining in each of the lobes of the plurality of lobes a lobar score for each of the radiographic features measured;

combining the lobar score of each of the lobes of the plurality of lobes to generate a radiograph lung score for each of the radiographic features measured;

comparing the radiograph lung score with a control radiograph lung score or a cut-off level for a corresponding radiographic feature; and predicting the transplant suitability of the donor lung and/or patient outcome following transplant of the donor lung based on the comparison of the radiograph lung score with the control radiograph lung score or cut-off level, optionally based on differences or similarities between the radiograph lung score and the control radiograph lung score or cut-off level.

In at least one embodiment, each of the radiographic features measured in each of the lobes of the plurality of lobes is attributed a score of 0, 1, 2 or 3, 0 indicating an absence of the radiographic feature, 1 being indicating a mild level of the radiographic feature, 2 indicating a moderate level of the radiographic feature and 3 indicating a severe level of the radiographic feature.

In at least one embodiment, the score of 1 indicates the radiographic feature occupies less than one third of the lobar volume, the score of 2 indicates the radiographic feature occupies one third to two thirds of the lobar volume and the score of 3 indicates the radiographic feature occupies more than two thirds of the lobar volume.

The method can comprise measuring 3, 4 or 5 radiographic features. In at least one embodiment the radiographic features comprise consolidation and infiltrate. In at least one embodiment, the radiographic features comprise consolidation, infiltrate and interstitial line.

In at least one embodiment, the patient outcome is selected from number of days of mechanical ventilation, ICU length of stay, hospital length of stay, APACHE score and post graft dysfunction (PGD) grade, optionally PGD0/1, PGD2 or PGD3.

The radiographic features can be measured in one or more lobes, for example 3, 4 or all 6 lobes.

In at least one embodiment, the method comprises measuring the radiographic feature of consolidation in the 6 lobes, wherein the radiograph lung score for consolidation of less than 8, less than 7, less than 6, less than 5, less than 4 or less than 3 is indicative the donor lung is likely suitable for transplant and/or the patient is likely to have a good outcome following transplant. In embodiments where less than 6 lobes are assessed, for example 3 lobes, a radiograph lung score for consolidation of less than 4 or less than 3.5 or less than 3 or less than 2 or less than 1.5 is indicative the donor lung is likely suitable for transplant and/or the patient is likely to have a good outcome following transplant.

In at least one embodiment, the method comprises measuring the radiographic feature of infiltrate in the 6 lobes, wherein the radiograph lung score for infiltrate of less than 8, less than 7, less than 6, less than 5, less than 4 or less than 3 is indicative the donor lung is likely suitable for transplant and/or the patient is likely to have a good outcome following transplant. In embodiments where less than 6 lobes are assessed, for example 3 lobes, a radiograph lung score for infiltrate of less than 4 or less than 3 or less than 2.5 or less than 2 or less than 1.5 is indicative the donor lung is likely suitable for transplant and/or the patient is likely to have a good outcome following transplant.

In at least one embodiment, the method comprises measuring the radiographic feature of atelectasis in the 6 lobes, wherein the radiograph lung score for atelectasis of less than 2, than 1.5, less than 1 or less than 0.5 is indicative the donor lung is likely suitable for transplant and/or the patient is likely to have a good outcome following transplant. In embodiments where less than 6 lobes are assessed, for example 3 lobes, a radiograph lung score for atelectasis of less than 1 or less than 0.75 or less than 0.5 or less than 0.25 is indicative the donor lung is likely suitable for transplant and/or the patient is likely to have a good outcome following transplant.

In at least one embodiment, the method comprises measuring the radiographic feature of nodule in the 6 lobes, wherein the radiograph lung score for nodule of less than 2, than 1.5, less than 1 or less than 0.75 is indicative the donor lung is likely suitable for transplant and/or the patient is likely to have a good outcome following transplant. In embodiments where less than 6 lobes are assessed, for example 3 lobes, a radiograph lung score for nodule of less than 1 or less than 0.75 or less than 0.5 is indicative the donor lung is likely suitable for transplant and/or the patient is likely to have a good outcome following transplant.

In at least one embodiment, the method comprises measuring the radiographic feature of interstitial line in the 6 lobes, wherein the lung score for interstitial line of less than 6, than 5, less than 4 or less than 3 is indicative the donor lung is likely suitable for transplant and/or the patient is likely to have a good outcome following transplant. In embodiments where less than 6 lobes are assessed, for example 3 lobes, a radiograph lung score for interstitial line of less than 3 or less than 2 or less than 1 or less than 0.5 is indicative the donor lung is likely suitable for transplant and/or the patient is likely to have a good outcome following transplant.

The good outcome following transplant can comprise three days or less of mechanical ventilation and/or being free from a graft-related death causes within 30 days, primary graft dysfunction grade 3 (PGD3), extracorporeal life support, extracorporeal membrane oxygenation and/or prolonged hospital/ICU stays.

In at least one embodiment, the donor lung measuring as likely suitable for transplant is subsequently transplanted into the patient.

In at least one embodiment, the method comprises measuring the radiographic feature of consolidation in the 6 lobes, wherein the radiograph lung score for consolidation of greater than 8, greater than 9, greater than 10 or greater than 11 is indicative the donor lung is likely not suitable for transplant and/or the patient is likely to have a poor outcome following transplant. In embodiments where less than 6 lobes are assessed, for example 3 lobes, a radiograph lung score for consolidation of greater than 4, greater than 4.5, greater than 5 or greater than 5.5 is indicative the donor lung is likely not suitable for transplant and/or the patient is likely to have a poor outcome following transplant.

In at least one embodiment, the method comprises measuring the radiographic feature of infiltrate in the 6 lobes, wherein the radiograph lung score for infiltrate of greater than 8, greater than 9, greater than 10 or greater than 11 is indicative the donor lung is likely not suitable for transplant and/or the patient is likely to have a poor outcome following transplant. In embodiments where less than 6 lobes are assessed, for example 3 lobes, a radiograph lung score for infiltrate of greater than 4, greater than 4.5, greater than 5 or greater than 5.5 is indicative the donor lung is likely not suitable for transplant and/or the patient is likely to have a poor outcome following transplant.

In at least one embodiment, the method comprises measuring the radiographic feature of atelectasis in the 6 lobes, wherein the radiograph lung score for atelectasis of greater than 2, greater than 3, greater than 4 or greater than 5 is indicative the donor lung is likely not suitable for transplant and/or the patient is likely to have a poor outcome following transplant. In embodiments where less than 6 lobes are assessed, for example 3 lobes, a radiograph lung score for atelectasis of greater than 1, greater than 1.5, greater than 2 or greater than 2.5 is indicative the donor lung is likely not suitable for transplant and/or the patient is likely to have a poor outcome following transplant.

In at least one embodiment, the method comprises measuring the radiographic feature of nodule in the 6 lobes, wherein the radiograph lung score for nodule of greater than 2, greater than 3, greater than 4 or greater than 5 is indicative the donor lung is likely not suitable for transplant and/or the patient is likely to have a poor outcome following transplant. In embodiments where less than 6 lobes are assessed, for example 3 lobes, a radiograph lung score for nodule of greater than 1, greater than 1.5, greater than 2 or greater than 2.5 is indicative the donor lung is likely not suitable for transplant and/or the patient is likely to have a poor outcome following transplant.

In at least one embodiment, the method comprises measuring the radiographic feature of interstitial line in the 6 lobes, wherein the radiograph lung score for interstitial line of greater than 6, greater than 7, greater than 8 or greater than 9 is indicative the donor lung is likely not suitable for transplant and/or the patient is likely to have a poor outcome following transplant. In embodiments where less than 6 lobes are assessed, for example 3 lobes, a radiograph lung score for interstitial line of greater than 3, greater than 3.5, greater than 4 or greater than 4.5 is indicative the donor lung is likely not suitable for transplant and/or the patient is likely to have a poor outcome following transplant. The poor outcome following transplant can be prolonged mechanical ventilation, optionally greater than three days, a graft-related death causes within 30 days, PGD3, extracorporeal life support, extracorporeal membrane oxygenation and/or prolonged hospital/ICU stays.

In at least one embodiment, the donor lung predicted as not likely suitable for transplant is declined for transplant or subject to further perfusion and optionally an assessment of radiographic features in a radiograph of a lung at a later time point including 1 hour, 2 hours or 3 hours following initial assessment.

In at least one embodiment, the method further comprises first obtaining the radiograph of the donor lung. The obtaining may comprise retrieving or receiving a digital image and/or taking the radiograph for example with an X-ray imaging device.

The radiograph can be obtained for a lung undergoing during EVLP, for example after a certain amount of EVLP, for example at least 15 min, after retrieval, for example before start of EVLP or after EVLP has ceased.

In at least one embodiment, the radiograph of the lung is obtained after lung retrieval for example before starting EVLP.

In at least one embodiment, the donor lung is a donor lung undergoing EVLP.

Multiple radiographs can be obtained for example of a lung prior to EVLP, after 1 hour of EVLP and/or after 3 hours of EVLP.

In at least one embodiment, the radiograph is of a lung obtained after about 15 minutes of EVLP, 30 minutes of EVLP, about 1 hour of EVLP, about 2 hours of EVLP, about 3 hours of EVLP or about 4 hours of EVLP.

In at least one embodiment, the radiograph obtained is of a lung during EVLP, while the donor lung is in the EVLP machine. The radiograph may be taken for example after about 15 minutes of EVLP, 30 minutes of EVLP, about 1 hour of EVLP, about 2 hours of EVLP, about 3 hours of EVLP or about 4 hours of EVLP.

In at least one embodiment, the method or at least a step thereof is computer-implemented.

In another aspect, in accordance with the teachings herein, there is provided at least one embodiment of a computer-implemented method for predicting transplant suitability of an ex vivo donor lung optionally undergoing ex vivo lung perfusion (EVLP) and/or patient outcome following transplant of the donor lung, wherein the method is performed by at least one processor and the method comprises: obtaining measurements of at least two radiographic features in a plurality of lobes of the donor lung from a radiograph of the donor lung, the radiographic features optionally selected from consolidation, infiltrate, atelectasis, nodule and interstitial line, and the plurality of lobes selected from right upper lobe, right middle lobe, right lower lobe, left upper lobe, lingula and left lower lobe; determining in each of the lobes of the plurality of lobes a lobar score for each of the radiographic features measured; combining the lobar score of each of the lobes of the plurality of lobes to generate a radiograph lung score for each of the radiographic features measured; comparing the radiograph lung score with a control radiograph lung score or a cut-off level for a corresponding radiographic feature; and predicting the transplant suitability of the donor lung and/or patient outcome following transplant of the donor lung based on the comparison of the radiograph lung score with the control radiograph lung score or cut-off level, optionally based on differences or similarities between the radiograph lung score and the control radiograph lung score or cut-off level.

The computer-implemented method may be further defined according to any one of the embodiments described herein.

In another aspect, in accordance with the teachings herein, there is provided at least one embodiment of a computer implemented method for predicting transplant suitability of an ex vivo donor lung optionally undergoing ex vivo lung perfusion (EVLP) and/or patient outcome following transplant of the donor lung, wherein the method is performed by at least one processor and the method comprises: obtaining measurements of at least one or at least two radiographic feature(s) in a plurality of lobes of the donor lung from a radiograph of the donor lung, the radiographic features optionally selected from consolidation, infiltrate, atelectasis, nodule and interstitial line, and the plurality of lobes selected from right upper lobe, right middle lobe, right lower lobe, left upper lobe, lingula and left lower lobe; determining in each of the lobes of the plurality of lobes a lobar score for each of the radiographic features measured; combining the lobar score of each of the lobes of the plurality of lobes to generate a radiograph lung score for each of the radiographic features measured; and predicting the transplant suitability of the donor lung and/or patient outcome following transplant of the donor lung by providing the radiograph lung score for each of the radiographic features measured to a prediction model.

In at least one embodiment, the ex vivo lung is a lung undergoing ex vivo lung perfusion (EVLP).

In at least one embodiment of a computer-implemented method, the computer-implemented method may further comprise displaying and/or storing an output related to predicting the transplant suitability of an ex vivo donor lung optionally undergoing ex vivo lung perfusion (EVLP) and/or patient outcome following transplant of the donor lung.

In at least one embodiment, the prediction model is an RLS model that compares a Radiograph Lung Score (RLS) to a control radiograph lung score or cut-off level for each radiographic feature to predict transplant suitability of an ex vivo donor lung optionally undergoing ex vivo lung perfusion and/or patient outcome following transplant of the donor lung.

In at least one embodiment, the prediction model is a univariate regression model that is determined for the radiographic features measured.

In at least one embodiment, the prediction model is a multivariate regression model that is determined for two or more of the radiographic features measured.

In at least one embodiment, the prediction model is a multivariate regression model that is determined for one or more physiological measurements of the donor lung and for two or more of the radiographic features measured.

In at least one embodiment, the physiological measurements include oxygenation and/or edema.

In at least one embodiment, the prediction model is a machine learning model including a decision tree, or a neural network.

In at least one embodiment, AI-guided image analysis is performed on one or more x-ray images of the donor lung in the EVLP to determine one or more image-based features that are provided as input into the prediction model.

In at least one embodiment, the predicted transplant suitability of a donor lung undergoing ex vivo lung perfusion is classified as transplanted versus declined donor lungs.

In at least one embodiment, the predicted patient outcome following transplant of the donor lung is classified as based on various recipient mechanical ventilation outcomes.

In at least one embodiment, one of the prediction models described herein may be used to provide a predicted probability for two or more outcome classifications.

In another aspect, in accordance with the teachings herein, there is provided at least one embodiment of a device for predicting transplant suitability of an ex vivo donor lung optionally undergoing ex vivo lung perfusion (EVLP) and/or patient outcome following transplant of the donor lung, wherein the device comprises: a memory for storing program instructions; and at least one processor that is communicatively coupled to the memory, the at least one processor being configured, when executing the program instructions, to perform the method according to any one of the embodiments described herein.

In another aspect, in accordance with the teachings herein, there is provided at least one embodiment of a system for predicting transplant suitability of an ex vivo donor lung optionally undergoing ex vivo lung perfusion (EVLP) and/or patient outcome following transplant of the donor lung, wherein the system comprises the device defined according to any one of the embodiments described herein; and an EVLP platform, optionally an EVLP platform, that is adapted to store the donor lung.

In at least one embodiment, the system further comprises an x-ray imaging device and optionally one or more sensors.

In another aspect, in accordance with the teachings herein, there is provided at least one embodiment of a non-transitory computer-readable storage medium storing computer-readable instructions that, when executed by at least one processor of an electronic device, configure the electronic device to perform a method for predicting transplant suitability of an ex vivo donor lung optionally undergoing ex vivo lung perfusion (EVLP) and/or patient outcome following transplant of the donor lung, wherein the method is defined according to any one of the embodiments described herein.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 4C shows an EVLP radiograph in different donor lungs at 1 hour demonstrating a moderate amount of opacity in right mid lung (*) predominantly characterized as consolidation and surrounding infiltrate. FIG. 4D shows a magnified EVLP radiograph at 1 hour demonstrating Kerley B lines (arrows) in the periphery of the left upper lobe.

FIG. 11A shows the tubing overlying the lower lung that can appear as lung nodules (identified by short arrows) and linear atelectasis in the left upper lobe (long arrow). FIG. 11B shows the honeycomb-like artifact overlying the upper left lobe and extending beyond the lung (arrows) into the EVLP basis.

Figure 1B:
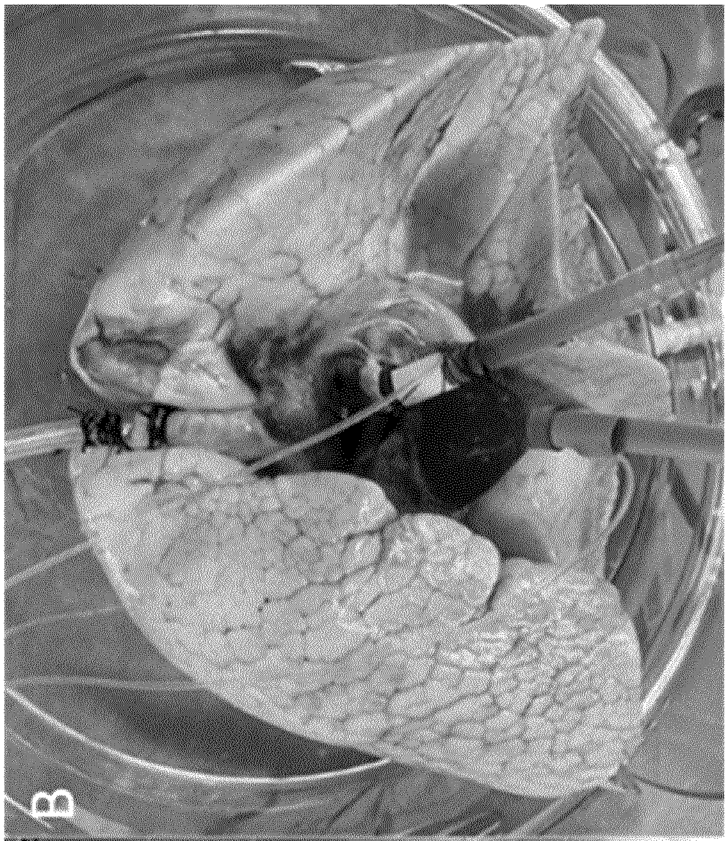
FIGS. 1A and 1B are images showing a donor lung ex vivo lung perfusion radiograph (FIG. 1A) and the corresponding donor lung photograph (FIG. 1B). An endotracheal tube and the two cannulas for arterial and venous circulation can be seen.

Further aspects and features of the example embodiments described herein will appear from the following description taken together with the accompanying drawings.

DETAILED DESCRIPTION OF THE DISCLOSURE

I. Definitions

The term "radiographic features" as used herein means one or more lung conditions or abnormalities that appear on radiographs of donor lungs optionally undergoing EVLP, including consolidation, infiltrates (also referred to as ground glass opacity), atelectasis, nodules, and interstitial lines. Such conditions or abnormalities in traditional chest X-rays are well-known and commonly used in the art, as defined for example in Hansell D M, Bankier A A, MacMahon H, McLoud T C, Muller N L and Remy J. Fleischner Society: glossary of terms for thoracic imaging. Radiology. 2008; 246:697-722, herein incorporated by reference in its entirety. It is believed that the identification and assessment of these features in lungs on an ex vivo circuit for example, isolated from the chest wall, has not been observed.

The term "lobar score" as used herein means a measurement of the severity of a radiographic feature as described herein in a lobe selected among right upper lobe, right middle lobe, right lower lobe, left upper lobe, lingula, and left lower lobe. The radiographic feature, e.g., consolidation, may for example be scored from 0 to 3 for each lobe where 0 represents the absence of the radiographic feature, 1 represents the radiographic feature occupying less than one third of the lobar volume (e.g., "mild"), 2 represents the radiographic feature occupying one-to two-thirds of the lobar volume (e.g., "moderate"), and 3 represents more than two-thirds of the lobar volume involved (e.g., "severe"). Other lobar scores for assessing the severity of a radiographic feature are also contemplated, for example from 0 to 2, 0 to 5 or 0 to 10.

The term "radiograph lung score", "radiographic lung score" or "RLS" as used herein means a score calculated by summing or the lobar score of each assessed lobe for a particular radiographic feature. For example, where the lobar score has a score from 0 to 3 and where the lobar score is assessed in all six lobes, the radiograph lung score has a minimum score of 0 and a maximum score of 18 for each radiographic feature.

The term "patient outcome" also referred to as "outcome" as used herein means one or more of primary graft dysfunction (PGD) grade, graft-related patient death, total hospital length of stay, transplant-related hospital length of stay, total intensive care unit (ICU) length of stay, transplant-related ICU length of stay, post-transplant ICU length of stay, APACHE score, days on mechanical ventilation, or patient-related use of extracorporeal membrane oxygenation (ECMO).

The terms "control radiograph lung score" and "cut-off level" as used herein refer to a comparator score or threshold value for a radiographic feature with known transplant suitability and/or patient outcome(s), to which the donor radiograph lung score can be compared, and a predetermined or selected threshold score based on known transplant suitability and/or patient outcome(s). For example, the control radiograph lung score or cut-off level is associated with an ex vivo donor lung, optionally an EVLP donor lung that is likely suitable for transplant or likely to have positive patient outcome(s) following transplant. For example, the control radiograph lung score or cut-off level is associated with an ex vivo lung, optionally an EVLP donor lung that is likely not suitable for transplant or likely to have negative patient outcome(s) following transplant. The "control radiograph lung score" and "cut-off level" may be determined using experimental data and statistical techniques.

The term "good outcome following transplant" or "poor outcome" as used herein means donor lungs which result in a good outcome in the recipient after transplantation. For example, good outcome may include being free from: graft-related death causes within 30 days, PGD3, extracorporeal life support/ECMO, prolonged hospital/ICU stays (for example, prolonged ICU stay can be greater than at least 3 days, for example greater than two weeks) or prolonged time spent on a mechanical ventilator. An ICU stay of 3 days or less can be considered a good outcome.

The term "poor outcome following transplant" or "poor outcome" as used herein means donor lungs which result in or induced poor outcome such as death from graft-related causes within 30 days, PGD3, requiring extracorporeal life support/ECMO, prolonged hospital/ICU stays, or prolonged time on mechanical ventilation. Examples of a poor outcome include a graft that after transplanting would result in a patient requiring an extended ICU stay (for example greater than 3 days or greater than two-weeks), as well as a graft that has an increased risk of having a PGD3 lung post-transplant.

The term "Acute Physiology And Chronic Health Evaluation Score" or "APACHE score" as used herein refers to an initial risk classification system for severely ill hospitalized patients. For example, it is applied within 24 hours of admission of a patient to an ICU. An integer score is computed based on several measurements, and higher scores correspond to more severe disease and a higher risk of death. For example, the point score is calculated from a patient's age and 12 routine physiological measurements: $AaDO_2$ or $PaO_2$ (depending on FiO2); temperature (rectal); mean arterial pressure; pH arterial; heart rate; respiratory rate; sodium (serum); potassium (serum); creatinine hematocrit; white blood cell count; and Glasgow Coma Scale. The score can also take into account whether the patient has acute renal failure, and whether prior to hospital admission the patient has severe organ system insufficiency or is immunocompromised.

The term "declined for transplant" as used herein means donor lungs that are declined for transplant, optionally donor lungs declined for transplant after EVLP. Such lungs can be discarded and/or used for research or other purposes. Lungs are presently typically declined for example if gas exchange function is not acceptable, represented by a partial pressure of oxygen less than 350 mmHg with a fraction of inspired oxygen of 100%; or 15% worsening of lung compliance compared to 1 h EVLP; or 15% worsening of pulmonary vascular resistance compared to 1 h EVLP; or development of significant edema; or worsening of ex vivo x-ray. As described herein, lungs are declined during or at the end of the EVLP process if comparison between the radiograph lung score of a radiographic feature is greater than a control radiograph lung score or cut-off level of the corresponding radiographic feature.

The term "suitability for transplant" as used herein means an organ that is predicted to be a good outcome donor lung, for example to have a decreased risk of a prolonged ICU (e.g., greater than 3 days, greater than 14 days) stay post-transplant. For example, a lung that would be predicted to involve 3 days or less of ICU stay for the recipient, may be considered a particularly suitable lung for transplant. As another example, a lung that may be predicted to involve 14 days or less of ICU stay for the recipient, may be considered a suitable lung for transplant.

The term "donor lung" and "lung" may be used interchangeably and may refer to one lung or a set.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed ended terms that specify the presence of stated features, elements, components, groups, integers, and/or steps, and also exclude the presence of other unstated features, elements, components, groups, integers and/or steps.

Further, terms of degree such as "substantially", "about" and "approximately" as used herein mean a reasonable amount of deviation of the modified term such that the end result is not significantly changed. These terms of degree should be construed as including a deviation of about +/−0.5%, about +/−1%, about +/−2%, about +/−5%, about +/−10% or about +/−15% of the modified term if this deviation would not negate the meaning of the word it modifies.

As used in this specification and the appended claims, the singular forms “a”, “an” and “the” include plural references unless the content clearly dictates otherwise. Thus, for example, a composition containing “a compound” includes a mixture of two or more compounds. It should also be noted that the term “or” is generally employed in its sense including “and/or” unless the content clearly dictates otherwise.

The definitions and embodiments described in particular sections are intended to be applicable to other embodiments herein described for which they are suitable as would be understood by a person skilled in the art.

The recitation of numerical ranges by endpoints herein includes all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term “about”, as described above.

Further, the definitions and embodiments described in particular sections are intended to be applicable to other embodiments herein described for which they are suitable as would be understood by a person skilled in the art. For example, in the following passages, different aspects of the disclosure, are defined in more detail. Each aspect so defined may be combined with any other aspect or aspects unless clearly indicated to the contrary. In particular, any feature indicated as being preferred or advantageous may be combined with any other feature or features indicated as being preferred or advantageous as long as it results in an operable combination (e.g., works properly and provides utility).

Various embodiments in accordance with the teachings herein will be described below to provide examples of at least one embodiment of the claimed subject matter. No embodiment described herein limits any claimed subject matter. The claimed subject matter is not limited to methods, devices, or systems having all of the features of any one of the methods, devices, or systems described below or to features common to multiple or all of the methods, devices, or systems described herein. It is possible that there may be a method, device, or system described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It should also be noted that, as used herein, the wording “and/or” is intended to represent an inclusive-or. That is, “X and/or Y” is intended to mean X or Y or both, for example. As a further example, “X, Y, and/or Z” is intended to mean X or Y or Z or any combination thereof.

A portion of the example embodiments of the methods, systems, or devices described in accordance with the teachings herein may be implemented as a combination of hardware or software. For example, a portion of the embodiments described herein may be implemented, at least in part, by using one or more computer programs, executing on one or more programmable devices comprising at least one processing element, and at least one data storage element (including volatile and non-volatile memory). These devices may also have at least one input device (e.g., a keyboard, a mouse, a touchscreen, and the like) and at least one output device (e.g., a display screen, a printer, a wireless radio, and the like) depending on the nature of the device. For example, and without limitation, the device may be programmable logic hardware, a mainframe computer, server, and personal computer, cloud based program or system, laptop, personal data assistance, cellular telephone, smartphone, or tablet device.

In addition, throughout this specification and the appended claims the term “communicative” as in “communicative pathway,” “communicative coupling,” and in variants such as “communicatively coupled,” is generally used to refer to any engineered arrangement for transferring and/or exchanging information. Examples of communicative pathways include, but are not limited to, electrically conductive pathways (e.g., electrically conductive wires, physiological signal conduction), electromagnetically radiative pathways (e.g., radio waves), or any combination thereof. Examples of communicative couplings include, but are not limited to, electrical couplings, magnetic couplings, radio couplings, or any combination thereof.

It should also be noted that there may be some elements that are used to implement at least part of the embodiments described herein that may be implemented via software that is written in a high-level procedural language such as object-oriented programming. The program code may be written in C, C++ or any other suitable programming language and may comprise modules or classes, as is known to those skilled in object-oriented programming. Alternatively, or in addition thereto, some of these elements implemented via software may be written in assembly language, machine language, or firmware as needed.

At least some of the software programs used to implement at least one of the embodiments described herein may be stored on a storage media or a device that is readable by a programmable device. The software program code, when read by the programmable device, configures the programmable device to operate in a new, specific and predefined manner in order to perform at least one of the methods described herein.

Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be described in the examples herein. Any method, software application or software module herein described may be implemented using computer readable/executable instructions that may be stored or otherwise held by such computer readable media and executed by the one or more processors.

It should also be noted that a description of an embodiment with several components in communication with each other does not imply that all such components are required. On the contrary a variety of optional components are described to illustrate the wide variety of possible embodiments in accordance with the teachings herein.

Further, although process steps, method steps, algorithms or the like may be described (in the disclosure and/or in the claims) in a sequential order, such processes, methods and algorithms may be configured to work in alternate orders. In other words, any sequence or order of steps that may be described does not necessarily indicate a requirement that the steps be performed in that order. The steps of processes described herein may be performed in any order that is practical and provides utility. Further, some steps may be performed simultaneously depending on the situation.

II Methods

Disclosed herein are radiographic features derived from lung radiographs that can be used to assess whether a donor lung undergoing is suitable for transplant and/or to predict patient outcomes following transplant with the donor lung.

The inventors have identified several radiographic features that are differentially detected in EVLP treated donor lungs that are associated with and can be used to assess or predict donor lung suitability for transplant after EVLP and one or more patient outcomes following transplant with the EVLP treated donor lung. It is believed that the identification and assessment of these features in lungs on an ex vivo circuit for example, isolated from the chest wall, has not been realized previously. In another aspect, the inventors have identified a scoring method that may improve the predictive power of the assessment of the radiographic features described herein.

As described in Examples 1 and 2, in a retrospective study, the radiograph lung scores of radiographic features were found to be correlated with conventional EVLP metrics of oxygenation and pulmonary edema (measured through perfusate lost during EVLP) both of which are markers of lung injury, which in turn is a marker of transplant suitability. Univariate regressions were performed using the radiograph lung score of each radiographic feature to predict the surgeon's decision to transplant as well as recipient outcome in terms of mechanical ventilation days. It was found that compared to the conventional pulmonary edema and oxygenation metrics, the radiographic findings performed well in multivariate regression when classifying transplanted versus declined donor lungs as well as recipient mechanical ventilation outcomes.

In another aspect, the inventors have determined that the radiographic features from assessments made by radiologists may be provided as input to a machine learning model to provide the predictions described herein. In another aspect, the inventors have determined that the radiographic features may be added as inputs to a machine learning model, such as the InsighTx model, that uses other inputs including one or more of donor features, physiological features, and biochemical features, as described in Applicant's co-pending PCT patent application and described further herein.

In another aspect, as shown in Example 3, the radiographic features may be used to predict transplantation outcomes using a regression model or a machine learning model. In another aspect, the radiographic features may be added to existing machine learning models that incorporate other EVLP parameters as inputs to machine learning models (e.g., the InsighTx model), In another aspect, radiographic images which do not include scores from radiologists may be used as inputs to computer vision models/deep learning models to improve model performance for predicting donor lung outcomes.

An aspect of the present disclosure is a method for predicting transplant suitability of an ex vivo donor lung, optionally undergoing ex vivo lung perfusion (EVLP), and/or patient outcome following transplant of the donor lung, comprising:

measuring in a radiograph of the donor lung at least two radiographic features in a plurality of lobes of the donor lung, the radiographic features optionally selected from consolidation, infiltrate, atelectasis, nodule and interstitial line, and the plurality of lobes selected from right upper lobe, right middle lobe, right lower lobe, left upper lobe, lingula and left lower lobe;

determining in each of the lobes of the plurality of lobes a lobar score for each of the radiographic features measured;

combining the lobar score of each of the lobes of the plurality of lobes to generate a radiograph lung score for each of the radiographic features measured;

comparing the radiograph lung score with a control radiograph lung score or a cut-off level for a corresponding radiographic feature; and predicting the transplant suitability of the donor lung and/or patient outcome following transplant of the donor lung based on the comparison of the radiograph lung score with the control radiograph lung score or cut-off level, optionally based on differences or similarities between the radiograph lung score and the control radiograph lung score or cut-off level.

In such embodiments, the term "similarities" may be understood as meaning that lungs with good outcomes have similar RLS whereas lungs with bad outcomes have similar RLS. Further, the term "differences" may be understood as meaning that lungs with good outcomes and lungs with bad outcomes would have different RLS.

In at least one embodiment, if one feature appears unsuitable for transplant but all of the other features are suitable, the lungs may still be transplanted.

In at least one embodiment, the method further comprises first obtaining the radiograph of the ex vivo donor lung, optionally an ex vivo donor lung undergoing EVLP.

The lobar score of each radiographic feature measured provides a score of severity of the radiographic feature (e.g., consolidation).

The transplant suitability and/or patient outcome can be provided as a binary value such as suitable or not suitable, or a probability of an outcome such as a number or range for the probability that a subject post-transplant will be extubated within 72 hours or that a donor lung will be suitable for transplant, for example.

In at least one embodiment, the lobar score is determined by scoring the radiographic feature by its severity. For example, each of the radiographic features measured in each of the lobes of the plurality of lobes is attributed a score of 0, 1, 2 or 3, with 0 indicating an absence of the radiographic feature, 1 being indicating a mild level of the radiographic feature, 2 indicating a moderate level of the radiographic feature and 3 indicating a severe level of the radiographic feature. In at least one embodiment, the score of 1 may be used to indicate the radiographic feature occupies less than one third of the lobar volume, the score of 2 may be used to indicate the radiographic feature occupies one third to two thirds of the lobar volume and the score of 3 may be used to indicate the radiographic feature occupies more than two thirds of the lobar volume.

In at least one embodiment, the method comprises measuring at least 2 radiographic features. For example, the radiographic features may be, but are not limited to, consolidation and infiltrate.

In at least one embodiment, the method comprises measuring 3 radiographic features. The radiographic features are consolidation and infiltrate, and one of atelectasis, nodule and interstitial line; optionally: (a) consolidation, infiltrate and atelectasis, (b) consolidation, infiltrate and nodule or (c) consolidation, infiltrate and interstitial line.

In at least one embodiment, the method comprises measuring 4 radiographic features. The radiographic features are consolidation and infiltrate, and two of atelectasis, nodule and interstitial line; optionally: (a) consolidation, infiltrate, atelectasis and nodule, (b) consolidation, infiltrate, atelectasis and interstitial line or (c) consolidation, infiltrate, nodule and interstitial line.

In at least one embodiment, the method comprises measuring 5 radiographic features. For example, the 5 radiographic features comprise consolidation, infiltrate, atelectasis, nodule and interstitial line.

In at least one embodiment, the patient outcome comprises number of days of mechanical ventilation, ICU length of stay, hospital length of stay, APACHE score and post graft dysfunction (PGD) grade, optionally PGD0/1, PGD2, or PGD3.

In at least one embodiment, the patient outcome is number of days of mechanical ventilation.

In at least one embodiment, the outcome is ICU length of stay.

In at least one embodiment, the patient outcome is hospital length of stay.

In at least one embodiment, the patient outcome is APACHE score.

In at least one embodiment, the patient outcome is post graft dysfunction (PGD) grade, optionally PGD0/1, PGD2, or PGD3.

In at least one embodiment, the method of predicting is carried out by measuring one or more of the radiographic features described herein as well as with the measuring of conventional metrics such as pulmonary edema and/or oxygenation metrics.

In at least one embodiment, instead of using the XGBoost model (InsightTx is a type of XGBoost model), TabNet or neural additive models may be used.

The radiographic features can be measured in one or more lobes, for example 2, 3, 4, 5 or all 6 lobes. In at least one embodiment, the radiographic features are measured in 3 lobes among right upper lobe, right middle lobe, right lower lobe, left upper lobe, lingula, and left lower lobe. In at least one embodiment, the radiographic features are measured in 4 lobes among right upper lobe, right middle lobe, right lower lobe, left upper lobe, lingula, and left lower lobe. In at least one embodiment, the radiographic features are measured in 5 lobes among right upper lobe, right middle lobe, right lower lobe, left upper lobe, lingula, and left lower lobe. In at least one embodiment, the radiographic features are measured in 6 lobes. In at least one embodiment, the radiographic features are measured in the right lung e.g., in one or more of the right upper lobe, right middle lobe and right lower lobe. In at least one embodiment, the radiographic features are measured in the left lung such as, e.g., one or more of the left upper lobe, lingula, and left lower lobe.

In at least one embodiment, the method comprises measuring the radiographic feature of consolidation in the 6 lobes, wherein the radiograph lung score for consolidation of less than a cut-off level of about 8 is indicative the donor lung is likely suitable for transplant and/or the patient is likely to have a good outcome following transplant. In at least one embodiment, the method comprises measuring the radiographic feature of consolidation in the 6 lobes, wherein the radiograph lung score for consolidation of less than a cut-off level of about 7 is indicative the donor lung is likely suitable for transplant and/or the patient is likely to have a good outcome following transplant. In at least one embodiment, the method comprises measuring the radiographic feature of consolidation, in the 6 lobes, wherein the radiograph lung score for consolidation of less than a cut-off level of about 6 is indicative the donor lung is likely suitable for transplant and/or the patient is likely to have a good outcome following transplant. In at least one embodiment, the method comprises measuring the radiographic feature of consolidation in the 6 lobes, wherein the radiograph lung score for consolidation of less than a cut-off level of about 5 is indicative the donor lung is likely suitable for transplant and/or the patient is likely to have a good outcome following transplant. In at least one embodiment, the method comprises measuring the radiographic feature of consolidation in the 6 lobes, wherein the radiograph lung score for consolidation of less than a cut-off level of about 4 is indicative the donor lung is likely suitable for transplant and/or the patient is likely to have a good outcome following transplant. In at least one embodiment, the method comprises measuring the radiographic feature of consolidation in the 6 lobes, wherein the radiograph lung score for consolidation of less than a cut-off level of about 3 is indicative the donor lung is likely suitable for transplant and/or the patient is likely to have a good outcome following transplant. In embodiments where fewer lobes are assessed, the cut off value is less, for example proportionately less.

In at least one embodiment, the method comprises measuring the radiographic feature of infiltrate in the 6 lobes, wherein the radiograph lung score for infiltrate of less than 8 is indicative the donor lung is likely suitable for transplant and/or the patient is likely to have a good outcome following transplant. In at least one embodiment, the method comprises measuring the radiographic feature of infiltrate in the 6 lobes, wherein the radiograph lung score for infiltrate of less than a cut-off level of about 7 is indicative the donor lung is likely suitable for transplant and/or the patient is likely to have a good outcome following transplant. In at least one embodiment, the method comprises measuring the radiographic feature of infiltrate in the 6 lobes, wherein the radiograph lung score for infiltrate of less than a cut-off level of about 6 is indicative the donor lung is likely suitable for transplant and/or the patient is likely to have a good outcome following transplant. In at least one embodiment, the method comprises measuring the radiographic feature of infiltrate in the 6 lobes, wherein the radiograph lung score for infiltrate of less than a cut-off level of about 5 is indicative the donor lung is likely suitable for transplant and/or the patient is likely to have a good outcome following transplant. In at least one embodiment, the method comprises measuring the radiographic feature of infiltrate in the 6 lobes, wherein the radiograph lung score for infiltrate of less than a cut-off level of about 4 is indicative the donor lung is likely suitable for transplant and/or the patient is likely to have a good outcome following transplant. In at least one embodiment, the method comprises measuring the radiographic feature of infiltrate in the 6 lobes, wherein the radiograph lung score for infiltrate of less than a cut-off level of about 3 is indicative the donor lung is likely suitable for transplant and/or the patient is likely to have a good outcome following transplant. In embodiments where fewer lobes are assessed, the cut off value is less, for example proportionately less.

In at least one embodiment, the method comprises measuring the radiographic feature of atelectasis in the 6 lobes, wherein the radiograph lung score for atelectasis of less than a cut-off level of about 2 is indicative the donor lung is likely suitable for transplant and/or the patient is likely to have a good outcome following transplant. In at least one embodiment, the method comprises measuring the radiographic feature of atelectasis, in the 6 lobes, wherein the radiograph lung score for atelectasis of less than a cut-off level of about 1.5 is indicative the donor lung is likely suitable for transplant and/or the patient is likely to have a good outcome following transplant. In at least one embodiment, the method comprises measuring the radiographic feature of atelectasis, in the 6 lobes, wherein the radiograph lung score for atelectasis of less than a cut-off level of about 1 is indicative the donor lung is likely suitable for transplant and/or the patient is likely to have a good outcome following transplant. In at least one embodiment, the method comprises measuring the radiographic feature of atelectasis in the 6 lobes, wherein the radiograph lung score for atelectasis of less than a cut-off level of about 0.5 is indicative the donor lung is likely suitable for transplant and/or the patient is likely to have a good outcome following transplant. In embodiments where fewer lobes are assessed, the cut off value is less, for example proportionately less.

In at least one embodiment, the method comprises measuring the radiographic feature of nodule in the 6 lobes, wherein the radiograph lung score for nodule of less than a cut-off level of about 2 is indicative the donor lung is likely suitable for transplant and/or the patient is likely to have a good outcome following transplant. In at least one embodiment, the method comprises measuring the radiographic feature of nodule, optionally in the 6 lobes, wherein the radiograph lung score for nodule of less than a cut-off level of about 1.5 is indicative the donor lung is likely suitable for transplant and/or the patient is likely to have a good outcome following transplant. In at least one embodiment, the method comprises measuring the radiographic feature of nodule, optionally in the 6 lobes, wherein the radiograph lung score for nodule of less than a cut-off level of about 1 is indicative the donor lung is likely suitable for transplant and/or the patient is likely to have a good outcome following transplant. In at least one embodiment, the method comprises measuring the radiographic feature of nodule, optionally in the 6 lobes, wherein the radiograph lung score for nodule of less than a cut-off level of about 0.75 is indicative the donor lung is likely suitable for transplant and/or the patient is likely to have a good outcome following transplant. In embodiments where fewer lobes are assessed, the cut off value is less, for example proportionately less.

In at least one embodiment, the method comprises measuring the radiographic feature of interstitial line in the 6 lobes, wherein the radiograph lung score for interstitial line of less than a cut-off level of about 6 is indicative the donor lung is likely suitable for transplant and/or the patient is likely to have a good outcome following transplant. In at least one embodiment, the method comprises measuring the radiographic feature of interstitial line in the 6 lobes, wherein the radiograph lung score for interstitial line of less than a cut-off level of about 5 is indicative the donor lung is likely suitable for transplant and/or the patient is likely to have a good outcome following transplant. In at least one embodiment, the method comprises measuring the radiographic feature of interstitial line in the 6 lobes, wherein the radiograph lung score for interstitial line of less than a cut-off level of about 4 is indicative the donor lung is likely suitable for transplant and/or the patient is likely to have a good outcome following transplant. In at least one embodiment, the method comprises measuring the radiographic feature of interstitial line in the 6 lobes, wherein the radiograph lung score for interstitial line of less than a cut-off level of about 3 is indicative the donor lung is likely suitable for transplant and/or the patient is likely to have a good outcome following transplant. In embodiments where fewer lobes are assessed, the cut off value is less, for example proportionately less.

In at least one embodiment, the good outcome following transplant comprises three days or less of mechanical ventilation and/or being free from a graft-related death causes within 30 days, primary graft dysfunction grade 3 (PGD3), extracorporeal life support, extracorporeal membrane oxygenation and/or prolonged hospital/ICU stays. In at last one embodiment, the good outcome following transplant is three days of less of mechanical ventilation.

In at least one embodiment, the donor lung measuring as likely suitable for transplant is subsequently transplanted into the patient.

In at least one embodiment, the method comprises measuring the radiographic feature of consolidation in the 6 lobes, wherein the radiograph lung score for consolidation of greater than a cut-off level of about 8 is indicative the donor lung is likely not suitable for transplant and/or the patient is likely to have a poor outcome following transplant. In at least one embodiment, the method comprises measuring the radiographic feature of consolidation in the 6 lobes, wherein the radiograph lung score for consolidation of greater than a cut-off level of about 9 is indicative the donor lung is likely not suitable for transplant and/or the patient is likely to have a poor outcome following transplant. In at least one embodiment, the method comprises measuring the radiographic feature of consolidation in the 6 lobes, wherein the radiograph lung score for consolidation of greater than a cut-off level of about 10 is indicative the donor lung is likely not suitable for transplant and/or the patient is likely to have a poor outcome following transplant. In at least one embodiment, the method comprises measuring the radiographic feature of consolidation in the 6 lobes, wherein the radiograph lung score for consolidation of greater than a cut-off level of about 11 is indicative the donor lung is likely not suitable for transplant and/or the patient is likely to have a poor outcome following transplant. In at least one embodiment, the method comprises measuring the radiographic feature of consolidation in the 6 lobes, wherein the radiograph lung score for consolidation of greater than a cut-off level of about 12 is indicative the donor lung is likely not suitable for transplant and/or the patient is likely to have a poor outcome following transplant. In embodiments where fewer lobes are assessed, the cut off value is less, for example proportionately less.

In at least one embodiment, the method comprises measuring the radiographic feature of infiltrate in the 6 lobes, wherein the radiograph lung score for infiltrate of greater than a cut-off level of about 8 is indicative the donor lung is likely not suitable for transplant and/or the patient is likely to have a poor outcome following transplant. In at least one embodiment, the method comprises measuring the radiographic feature of infiltrate in the 6 lobes, wherein the radiograph lung score for infiltrate of greater than a cut-off level of about 9 is indicative the donor lung is likely not suitable for transplant and/or the patient is likely to have a poor outcome following transplant. In at least one embodiment, the method comprises measuring the radiographic feature of infiltrate in the 6 lobes, wherein the radiograph lung score for infiltrate of greater than a cut-off level of about 10 is indicative the donor lung is likely not suitable for transplant and/or the patient is likely to have a poor outcome following transplant. In at least one embodiment, the method comprises measuring the radiographic feature of infiltrate in the 6 lobes, wherein the radiograph lung score for infiltrate of greater than a cut-off level of about 11 is indicative the donor lung is likely not suitable for transplant and/or the patient is likely to have a poor outcome following transplant. In embodiments where fewer lobes are assessed, the cut off value is less, for example proportionately less.

In at least one embodiment, the method comprises measuring the radiographic feature of atelectasis in the 6 lobes, wherein the radiograph lung score for atelectasis of greater than a cut-off level of about 2 is indicative the donor lung is likely not suitable for transplant and/or the patient is likely to have a poor outcome following transplant. In at least one embodiment, the method comprises measuring the radiographic feature of atelectasis in the 6 lobes, wherein the radiograph lung score for atelectasis of greater than a cut-off level of about 3 is indicative the donor lung is likely not suitable for transplant and/or the patient is likely to have a poor outcome following transplant. In at least one embodiment, the method comprises measuring the radiographic feature of atelectasis in the 6 lobes, wherein the radiograph lung score for atelectasis of greater than a cut-off level of about 4 is indicative the donor lung is likely not suitable for transplant and/or the patient is likely to have a poor outcome following transplant. In at least one embodiment, the method comprises measuring the radiographic feature of atelectasis in the 6 lobes, wherein the radiograph lung score for atelectasis of greater than a cut-off level of about 5 is indicative the donor lung is likely not suitable for transplant and/or the patient is likely to have a poor outcome following transplant. In embodiments where fewer lobes are assessed, the cut off value is less, for example proportionately less.

In at least one embodiment, the method comprises measuring the radiographic feature of nodule in the 6 lobes, wherein the radiograph lung score for nodule of greater than a cut-off level of about 2 is indicative the donor lung is likely not suitable for transplant and/or the patient is likely to have a poor outcome following transplant. In at least one embodiment, the method comprises measuring the radiographic feature of nodule in the 6 lobes, wherein the radiograph lung score for nodule of greater than a cut-off level of about 3 is indicative the donor lung is likely not suitable for transplant and/or the patient is likely to have a poor outcome following transplant. In at least one embodiment, the method comprises measuring the radiographic feature of nodule in the 6 lobes, wherein the radiograph lung score for nodule of greater than a cut-off level of about 4 is indicative the donor lung is likely not suitable for transplant and/or the patient is likely to have a poor outcome following transplant. In at least one embodiment, the method comprises measuring the radiographic feature of nodule in the 6 lobes, wherein the radiograph lung score for nodule of greater than a cut-off level of about 5 is indicative the donor lung is likely not suitable for transplant and/or the patient is likely to have a poor outcome following transplant. In embodiments where fewer lobes are assessed, the cut off value is less, for example proportionately less.

In at least one embodiment, the method comprises measuring the radiographic feature of interstitial line in the 6 lobes, wherein the radiograph lung score for interstitial line of greater than a cut-off level of about 6 is indicative the donor lung is likely not suitable for transplant and/or the patient is likely to have a poor outcome following transplant. In at least one embodiment, the method comprises measuring the radiographic feature of interstitial line in the 6 lobes, wherein the radiograph lung score for interstitial line of greater than a cut-off level of about 7 is indicative the donor lung is likely not suitable for transplant and/or the patient is likely to have a poor outcome following transplant. In at least one embodiment, the method comprises measuring the radiographic feature of interstitial line in the 6 lobes, wherein the radiograph lung score for interstitial line of greater than a cut-off level of about 8 is indicative the donor lung is likely not suitable for transplant and/or the patient is likely to have a poor outcome following transplant. In at least one embodiment, the method comprises measuring the radiographic feature of interstitial line in the 6 lobes, wherein the radiograph lung score for interstitial line of greater than a cut-off level of about 9 is indicative the donor lung is likely not suitable for transplant and/or the patient is likely to have a poor outcome following transplant. In embodiments where fewer lobes are assessed, the cut off value is less, for example proportionately less.

In at least one embodiment, the poor outcome following transplant is prolonged mechanical ventilation, optionally greater than three days, a graft-related death causes within about 30 days, PGD3, extracorporeal life support, extracorporeal membrane oxygenation and/or prolonged hospital/ICU stays.

In at least one embodiment, the donor lung predicted as not likely suitable for transplant is declined for transplant or subject to further perfusion and/or other treatment and optionally reassessment of radiographic features in a radiograph of a lung at a later time point, e.g., about 1 hour, about 2 hours or about 3 hours following the first assessment.

In at least one embodiment, the radiograph is obtained for a lung after donor lung retrieval, for example prior to EVLP.

In at least one embodiment, the donor lung is a donor lung undergoing EVLP.

In at least one embodiment, the radiograph obtained is of a lung during EVLP, while the donor lung is in the EVLP machine/platform. The radiograph may be taken for example after about 15 minutes of EVLP, about 30 minutes of EVLP, about 1 hour of EVLP, about 2 hours of EVLP, about 3 hours of EVLP or about 4 hours of EVLP.

In at least one embodiment, the radiograph obtained is of a lung that has received at least about 15 minutes of EVLP. In at least one embodiment, the radiograph is of a lung after it has received about 30 minutes of EVLP. In at least one embodiment, the radiograph is of a lung after it has received about 1 hour of EVLP. In at least one embodiment, the radiograph obtained is of a lung after it has received about 1.5 hours of EVLP. In at least one embodiment, the radiograph obtained is of a lung after it has received about 2 hours of EVLP. In at least one embodiment, the radiograph obtained is of a lung after it has received about 2.5 hours of EVLP. In at least one embodiment, the radiograph obtained is of a lung after it has received about 3 hours of EVLP. In at least one embodiment, the radiograph obtained is of a lung after it has received about 3.5 hours of EVLP. In at least one embodiment, the radiograph is obtained after it has received about 4 hours of EVLP.

In at least one embodiment, the cut-off levels for the radiographic features described herein may be determined statistically based on experimental data as will be further described. For example, a statistical technique may be used to determine the cut-off level. Alternatively, a decision tree algorithm such as, but not limited to, an XGBoost model may be used where each radiographic feature is provided as an input with its own score, and the decision tree algorithm will process all of the features and scores and then map out the most probable classification outcome.

In at least one embodiment, the method or at least a step thereof is computer-implemented.

Figure 10:
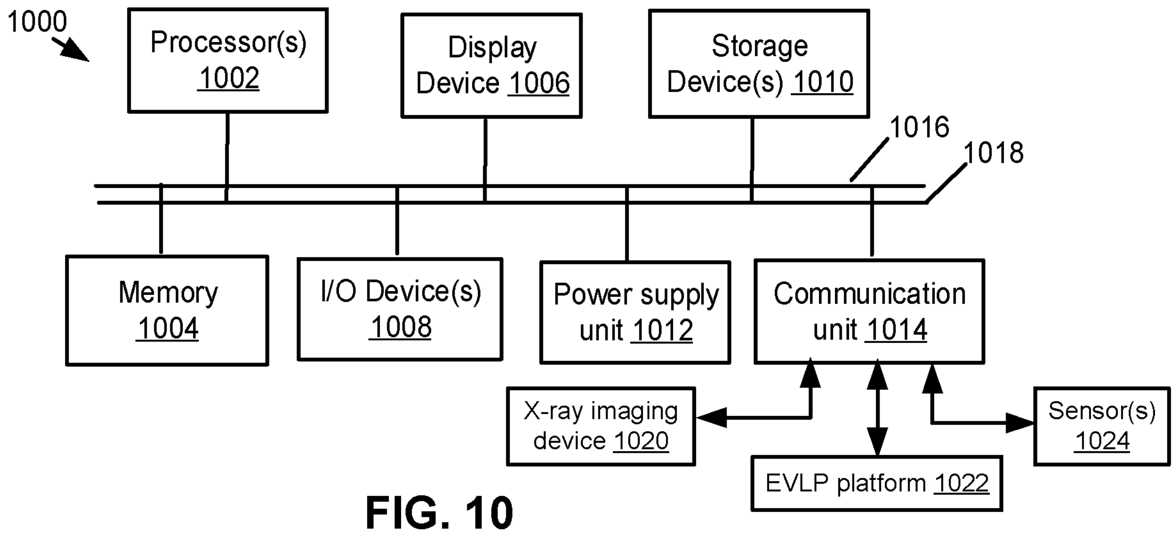
FIG. 10 shows an example embodiment of an electronic device for method for predicting transplant suitability of a donor lung undergoing ex vivo lung perfusion and/or patient outcome following transplant of the donor lung in accordance with the teachings herein.

Referring now to FIG. 10, shown therein is an example embodiment of an electronic device 1000 that may be used for predicting transplant suitability of a donor lung undergoing ex vivo lung perfusion and/or patient outcome following transplant of the donor lung in accordance with the teachings herein. The device 1000 may be implemented as a desktop computer, a tablet computer, a mobile device such as a smart phone, or any other suitable device capable of executing software. The electronic device 1000 may be used to implement any of the entities, methods, components or services described in the present subject matter.

The electronic device 1000 may include one or more processor ("processor(s)") 1002, memory 1004, a display device 1006, input/output (I/O) devices 1008 (e.g., a keyboard, at least one pointing device, a microphone, and/or a speaker), one or more storage devices 1010 (e.g., disk drives, USB keys), a power supply unit 1012 and a communication unit 1014 that may send and transmit data over an interconnect 1016 (e.g., communication bus and/or data bus) and receive power from a power bus 1018. The interconnect 1016 may represent any one or more separate physical buses, point to point connections, or both connected by appropriate bridges, adapters, or controllers that allow the various components 1002 to 1014 to communicate with one another. The interconnect 1016, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), 11C (12C) bus, or an Institute of Electrical and Electronics Components (IEEE) standard 1394 bus, also called "Firewire".

The processor(s) 1002 execute an operating system, and various software programs (also known as software modules), as described below in greater detail. In embodiments where there are two or more processors, these processors may function in parallel and perform certain functions. The processor(s) 1002 control the operation of the electronic device 1000 and in some embodiments other components of a system described below. The processor(s) 1002 may be any suitable processor(s), controller(s) or digital signal processor(s) that can provide sufficient processing power depending on the configuration and operational requirements of the electronic device 1000. For example, the processor(s) 1002 may include a high-performance processor. Alternatively, in at least one embodiment special-purpose hardwired (non-programmable) circuitry may be used, which may be in the form of, for example, one or more ASICs, PLDs, FPGAs, etc.

The memory 1004 and storage devices 1010 are computer-readable storage media that store software programs having software instructions that implement at least portions of the described embodiments. The memory 1004 generally includes RAM 114 and non-volatile storage. The RAM provides relatively responsive volatile storage to the processor(s) 1002. The non-volatile storage stores program instructions, including computer-executable instructions, for implementing the operating system and software modules (e.g., computer programs), as well as storing any data used by these software modules. The data may be stored in database or data files, such as for data relating to lungs and/or patients that are assessed using the electronic device 1000. The database/data files can be used to store data such as device settings, parameter values, and machine learning models. The database/data files can also store other data required for the operation of the electronic device such as dynamically linked libraries and the like. During operation of the electronic device 1000, the software instructions for the operating system, and the software modules, as well as any related data may be retrieved from the non-volatile storage and placed in RAM 114 to facilitate more efficient execution. The memory can also be used for storing temporary variables or other intermediate information during execution of instructions to be executed by the processor(s) 1002. Other computing structures and architectures may be used as appropriate.

The memory 1004 and storage devices 1010 are communicatively coupled to the electronic device 1000 so that the software instructions of the software programs stored on the memory 1004 and/or storage devices 1010 can be accessed and executed by the processor(s) 1002 of the electronic device 1000, which then configures the electronic device 1000 to perform one or more of the methods described in the present subject matter. In addition, the data structures and message structures may be stored or transmitted via a data transmission medium, such as a signal on a communications link. Various communications links may be used, such as the Internet, a local area network, a wide area network, or a point-to-point dial-up connection. Thus, computer readable media can include computer-readable storage media (e.g., "non-transitory" media) and computer-readable transmission media.

The software instructions stored in memory 1004 can be implemented using any appropriate software development environment or computer language such as high-level program code and/or firmware to configure the processor(s) 1002 to carry out actions described above. In some embodiments, such software or firmware may be initially provided to the electronic device 1000 by downloading it from a remote system via the communication unit 1014. In at least one embodiment, the software program may be provided as a packaged software product, a web-service, an API or any other means of software service.

The display device 1006 can be any suitable display that provides visual information depending on the configuration of the electronic device 1000. For instance, the display device 1006 can be a monitor and the like if the electronic device 1000 is a desktop computer. In other cases, the display device 1006 can be a display suitable for a laptop, tablet or handheld device such as an LCD-based display and the like. The display device 1006 can provide notifications to the user of the electronic device 1000. In some cases, the display device 1006 may be used to provide one or more GUIs through an Application Programming Interface. A user may then interact with the one or more GUIs for configuring the electronic device 1000 to operate in a certain fashion.

The I/O devices 1008 allow the user to provide input via an input device, which may be, for example, any combination of a mouse, a keyboard, a trackpad, a thumbwheel, a trackball, voice recognition, a touchscreen and the like depending on the particular implementation of the electronic device 1000. The I/O devices 1008 also include at least one output device that can be used to output information to the user, which may be, for example, any combination of the display device 1006, a printer or a speaker.

The power supply unit 1012 can be any suitable power source or power conversion hardware that provides power to the various components of the electronic device 101. The power supply unit 1012 may be a power adaptor or a rechargeable battery pack depending on the implementation of the electronic device 1000 as is known by those skilled in the art. In some cases, the power supply unit 1012 may include a surge protector that is connected to a mains power line and a power converter that is connected to the surge protector (both not shown). The surge protector protects the power supply unit 1012 from any voltage or current spikes in the main power line and the power converter converts the power to a lower level that is suitable for use by the various elements of the electronic device 1000. In other embodiments, the power supply unit 1012 may include other components for providing power or backup power as is known by those skilled in the art.

The communication unit 1014 allows the electronic device 1000 to communicate with other devices via a wired or wireless connection. Accordingly, the communication unit 1014 may include network adapters (e.g., network interfaces) for an Internet, Local Area Network (LAN), Ethernet, Firewire, modem or digital subscriber line connection. Alternatively, or in addition thereto, the communication unit 1014 may include a modem and/or a radio that may communicate utilizing CDMA, GSM, GPRS or Bluetooth protocol according to standards such as IEEE 802.11a, 802.11b, 802.11g, or 802.11n.

In at least one embodiment, there may be provided a system comprising the electronic device 1000 and an EVLP platform (not shown) that are communicatively coupled to one another. The EVLP platform is known to those skilled in the art.

In at least one embodiment, there may be provided a system comprising the electronic device 1000, an x-ray imaging device 1020 and an EVLP platform 1022 where the electronic device 1000 is communicatively coupled to the x-ray imaging device 1020 and the EVLP platform 1022. The x-ray imaging device 1020 is suitable for imaging a donor lung that is contained within the EVLP platform 1022. For example, the x-ray imaging device 1020 may be, but is not limited to, a DRX-Revolution mobile x-ray system.

In at least one embodiment, there may be provided a system comprising the electronic device 1000 and one or more sensors 1024 where the electronic device 1000 is communicatively coupled to sensor(s) 1024. The sensor(s) 1024 may be used to obtain data regarding lung. For example, the sensor(s) 1024 may be used to obtain ventilator data that may be used to measure certain lung parameters such as, but not limited to, compliance and/or airway pressure. In at least one embodiment, the sensor(s) 1024 may be used to obtain certain blood flow measurements for the lungs such as, but not limited to, real-time blood gas measurements. In at least one embodiment, the sensor(s) 1024 may be used to obtain both ventilator data and blood flow measurements from the donor.

Consistent with certain implementations of the present disclosure, results can be provided in response to the processor(s) 1002 executing one or more sequences of one or more software instructions contained in the memory 1004. Such software instructions can be read into memory 1004 from another computer-readable medium or computer-readable storage medium, such as the ROM and/or the storage device(s) 1010. Execution of the sequences of software instructions contained in the memory 1004 can cause the processor(s) 1002 to perform at least one of the methods/processes described herein. Alternatively hardwired circuitry can be used in place of or in combination with software instructions to implement the present teachings. Thus, implementations of the present teachings are not limited to any specific combination of hardware circuitry and software.

The term "computer-readable medium" (e.g., data store, data storage, etc.) or "computer-readable storage medium" as used herein refers to any media that participates in providing software instructions to the processor(s) 1002 for execution. Such a medium can take many forms, including but not limited to, non-volatile media, volatile media, and transmission media. Examples of non-volatile media can include, but are not limited to, optical, solid state, magnetic disks, such as the storage device(s) 1010. Examples of volatile media can include, but are not limited to, dynamic memory, such as memory 1004. Examples of transmission media can include, but are not limited to, coaxial cables, copper wire, and fiber optics, including the wires that include bus 1016. Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable media, data can be provided as signals on transmission media included in a communications apparatus or system to provide sequences of one or more instructions to the processor(s) 1002 of the electronic device 1000 for execution. For example, a communication apparatus may include a transceiver having signals that encode software instructions and data. The software instructions and data, when executed by the processor(s) 1002, configure the processor(s) 1002 to cause the processor(s) 1002 to implement one or more of the functions outlined in the disclosure herein. Representative examples of data communications transmission connections can include, e.g., telephone modem connections, wide area networks (WAN), local area networks (LAN), infrared data connections, NFC connections, etc.

It should be appreciated that the methodologies described herein, including flow charts, diagrams and accompanying disclosure can be implemented using the electronic device 1000 as a standalone device or on a distributed network of shared computer processing resources such as a cloud computing network.

In at least one embodiment, a computer-implemented method for predicting transplant suitability of a donor lung undergoing ex vivo lung perfusion and/or patient outcome following transplant of the donor lung or other methods described in accordance with the teachings herein as it relates to donor lungs in a recipient post-transplant can employ the use of a processor/device/system as disclosed in the present subject matter. For example, a computer device comprising a processor is coupled to a memory storing computer program code to implement one or more of the methods described in the present subject matter. The electronic device 1000 is also coupled to memory 1004 and/or to storage device(s) 1010 to access computer programs and data files including a data database for performing these methods. The electronic device 1000 may accept user input from a data input device, such as a keyboard, input data file, or network interface, or another system. The electronic device 1000 may provide an output to an output device such as a printer, the display device 1006, a network interface, or a data store which may be stored on the storage device(s) 1010.

In general, the program instructions stored in the memory 1004 and/or the storage device(s) 1010, when executed by the processor(s) 1002 configure the electronic device 1000 to obtain EVLP data and/or data related to lobar scores, radiograph lung scores, APACHE scores, oxygenation and/or edema determined from x-ray images and/or EVLP measurements via an input device and/or the communication unit 1014 or data obtained from the sensor(s) 1024. The data may be determined at various time intervals depending on the nature of the data where the time intervals include, for example, about 1 second, about 5 seconds, about 30 seconds, about 1 minute, about 5 minutes, about 10 minutes, about 15 minutes, about 30 minutes or about 1 hour. For example, the Xray images may be taken once or multiple times, during or after a period of EVLP (e.g., at about 1 and about 3 hours of EVLP);

whereas other EVLP measurements such as oxygenation, may be obtained at time intervals of about 1 second or less (e.g., continuous measurement).

Upon execution of the program instructions, the processor(s) 1002 is configured to then access a prediction model and associated model parameters and optionally comparison data, such as one or more control radiograph lung scores and/or one of more cut-off level(s) from the memory 1004 and/or the storage device(s) 1010, and executes the prediction model including providing at least some of the obtained data as input to the prediction model to obtain one or more outputs for predicting transplant suitability of a donor lung undergoing ex vivo lung perfusion and/or patient outcome following transplant of the donor lung. The output device may provide a visual output (e.g., on the display device 1006) or output data sent to another electronic device used by a medical professional) including one or more numbers, a graph; a score, etc. to indicate the prediction of transplant suitability of a donor lung undergoing ex vivo lung perfusion and/or patient outcome following transplant of the donor lung. This output may be used by a medical professional, such as a surgeon, to perform one or more actions described herein such as, but not limited to, proceeding with a transplant of the donor lung when a good outcome following transplant is predicted, for example.

In at least one embodiment, the prediction model may include an RLS model which may determine a radiograph lung score, as described herein, for various combinations of radiographic features (e.g., consolidation, infiltrates, atelectasis, nodules, and/or interstitial lines) and compare the RLS to a control radiograph lung score or cut-off level for each radiographic feature to predict transplant suitability of a donor lung undergoing ex vivo lung perfusion and/or patient outcome following transplant of the donor lung. Alternatively, in at least one embodiment, the radiograph lung scores for two or more radiograph features may be provided as inputs to a machine learning model to determine a prediction. For example, the machine learning model may be a decision tree or other machine-learning approaches described below.

In at least one embodiment, the prediction model may be a univariate regression model that is determined for a selected radiographic feature that is one of consolidation, infiltrates, atelectasis, nodules, or interstitial lines, for example. The prediction model is trained using training data from measurements for the selected radiographic feature to provide as output a predicted transplant suitability of a donor lung undergoing ex vivo lung perfusion and/or patient outcome following transplant of the donor lung.

In at least one embodiment, the prediction model may be a multivariate regression model that is determined for two or more selected radiographic features from the radiographic features of consolidation, infiltrates, atelectasis, nodules, and/or interstitial lines, for example. The prediction model is trained using training data from measurements for the selected radiographic features to provide as output a predicted transplant suitability of a donor lung undergoing ex vivo lung perfusion and/or patient outcome following transplant of the donor lung.

In at least one embodiment, the prediction model may be a multivariate regression model that is determined for one or more physiological measurements such as, but not limited to, any of the physiological measurements described herein, including oxygenation and/or edema, for example, and one or more selected radiographic features from the radiographic features of consolidation, infiltrates, atelectasis, nodules, and/or interstitial lines. The prediction model is trained using training data from measurements for the selected one or more physiological measurements and one or more radiographic features to provide as output a predicted transplant suitability of a donor lung undergoing ex vivo lung perfusion and/or patient outcome following transplant of the donor lung. For example, the multivariate regression model may include edema and oxygenation measurements and one of the radiograph lung scores.

In at least one embodiment, the various prediction models using the inputs described herein may be implemented using a machine learning model, statistical model, or other artificial intelligence technique. For example, the machine learning model may include, but is not limited to, a decision tree or a neural network. For example, in at least one embodiment computer vision models may be used including deep learning models such as, but not limited to, those based on convolutional neural networks and transformers. The deep learning models may be used to analyze radiograph images.

In at least one embodiment, the prediction model may incorporate image analysis and artificial intelligence for images obtained during ex vivo lung perfusion (EVLP). For example, AI-guided image analysis may be used to standardize image assessments during EVLP and detect patterns that are not observable by human observers. The images may be obtained using an x-ray imaging device 1020 and then used as inputs to an image analysis pipeline, where they can be automatically processed and interpreted by a neural network. Results of the image based analysis may be provided to the prediction model to allow surgeons to better assess which lungs are suitable for transplantation since the EVLP-based images capture isolated organs outside of the body and, thus, are relatively clean and unobstructed by muscle, bones, fluid, fat, and other features that otherwise add to the noise found in routine chest X-rays.

In at least one embodiment that uses AI-guided image analysis, the methodology may generally comprise: obtaining one or more x-ray images of a donor lung in an EVLP platform, analyzing the obtained image(s) using an AI-based image algorithm; and comparing the results of the AI-based image algorithm with a control database of images to perform an assessment on the donor lung. For example, the assessment may include a differential assessment indicative of lung injury. As previously mentioned, the x-ray imaging device 1020 may be a DRX-Revolution mobile x-ray system.

In at least one embodiment that use AI-guided image analysis, data may be obtained from the AI-based image algorithm that can be used as one or more input parameters to one or more of the prediction models described herein. For example, these one or more input parameters may include one or more aspects of lung injury assessment. Alternatively, in at least one embodiment, the features determined from the AI-based image algorithm may be added to or used along with other EVLP parameters such as physiological, biochemical, donor, recipient and/or biological measurements in another AI-based algorithm for determining a composite lung injury score that is associated with lung injury and predictive of post-transplant outcome for the recipient and/or to generate a prediction for transplant suitability of a donor lung undergoing ex vivo lung perfusion (EVLP) and/or patient outcome following transplant of the donor lung. Examples of models incorporating such parameters and machine learning models is described in Applicant's co-pending PCT patent application entitled "SYSTEMS AND METHODS FOR PREDICTING OUTCOMES FOR A LUNG UNDERGOING AN EX VIVO LUNG PERFUSION", which claims priority to U.S. provisional patent application No. 63/315,042 filed on Feb. 28, 2022, is hereby incorporated by reference in its entirety.

In at least one embodiment that use AI-guided image analysis, a Residual Neural Network (ResNet), which is one type of a convolutional neural network (CNN), may be used to train the prediction model to identify lung conditions or abnormalities that appear on EVLP radiographic images: such as atelectasis (collapsed lung), edema (excess fluid), pneumonia (infection), and/or infiltration and consolidation (presence of fluid or material). These conditions are used in clinical assessment and can be resolved on EVLP. The prediction model may be pre-trained using a large-scale public database (e.g., the Chest X-ray Dataset from NIH, MIMIC Chest X-ray from MIT, and CheXpert from Stanford University). With these datasets, which contain hundreds of thousands of images, the prediction model may be trained to specialize in specific lung features by learning general lung outlines, spatial structures, and pixel distributions to determine a suitable set of starting weights. Transfer learning may then be used where the prediction model is fine-tuned using EVLP images. Accordingly, the prediction model may be trained to recognize the presence of each lung condition on the whole image. In at least one embodiment, noise removal and fine-tuning of hyperparameters may be used to optimize classification performance and would be assessed using cross-validation. Additional methods/approaches that may be used include, but are not limited to, EfficientNet-B2, EfficientNet-B3, DenseNet-121, VGG-16, Inception v4, and Se-ResNext-50. In at least one embodiment, the prediction model may also apply semantic segmentation to recognize the specific boundaries and location of each condition in order to achieve granularity.

In embodiments which employ image analysis, the pipeline may be used to train an AI model such as a neural network model such as those provided in the "PyTorch" and "timm" code libraries that are available in the Python programming language. Furthermore, an image analysis pipeline often consists of a dataloader module, a model training module, and a classification module. In the dataloader module, data (i.e., image data) can be preprocessed, and image augmentations can be incorporated to optimize training. In the training module, the model architecture can be specified along with its settings. A performance metric can be included in the classification module, where the optimizer and validation method can be configured. These can be developed using platforms such as PyTorch or Tensorflow. Alternatively, a public library such as PyTorch Image Models (the acronym is timm) or Medical Open Network for Artificial Intelligence (MONAI) can be applied.

In at least one embodiment, for one of the prediction models described herein, the predicted transplant suitability of a donor lung undergoing ex vivo lung perfusion may be classified as transplanted versus declined donor lungs.

In at least one embodiment, for one of the prediction models described herein, the predicted patient outcome following transplant of the donor lung may be classified as various durations of recipient mechanical ventilation.

In at least one embodiment, where the prediction models described herein-may be used to provide a predicted probability for two or more outcome classifications, the machine learning model used for prediction may be a trained decision tree algorithm or a trained neural network. For example, when there are two output classes, a binary classifier may be used.

For each of the embodiments utilizing prediction models described herein, the input data may be obtained at specific times after the donor lung is inserted into the EVLP such as first hour measurements or first and third hour measurements, or some of the input data may be obtained on a real-time or quasi real-time bases, for example.

In at least one embodiment, a machine learning model may be used to generate a prediction for transplant suitability of an ex vivo donor lung optionally undergoing ex vivo lung perfusion (EVLP) and/or patient outcome following transplant of the donor lung from at least one radiograph of the donor lung. The machine learning model may have been trained on radiograph images labeled with one or more of the radiographic features discussed herein present in one or more lobes in radiographic training images and/or with scores associated with the radiographic features, as discussed above.

In at least one embodiment, the model is trained on radiograph images labeled with scores for at least two radiographic features.

IN at least one embodiment, at least some of the training images may be labeled with a metric, score, or other assessment of patient outcome following transplantation.

In at least one embodiment, a multi-stage machine learning model may include a first stage for identifying and generating an assessment (e.g., a score) for one or more radiographic features of one or more lobes in a radiograph of a donor lung and a second stage for generating a prediction for transplant suitability of a donor lung undergoing ex vivo lung perfusion (EVLP) and/or patient outcome following transplant of the donor lung based on the output from the first stage. In at least one embodiment, the second stage may generate a prediction based on other information in addition to the output from the first stage, including EVLP parameters such as any of the physiological, biochemical, and/or biological measurements discussed herein.

In at least one embodiment, the prediction is generated based on providing, in addition to at least two radiograph features, at least one physiological, biochemical, donor, recipient and/or biological as inputs to the machine learning model.

In at least one embodiment, the machine learning model comprises a deep learning model.

A computer-program product is also described herein. The computer-program product can be used in conjunction with an electronic device. The computer-program product can include a non-transitory computer-readable storage medium and/or a computer-program mechanism embedded therein. The computer-program product includes program instructions for performing any of the methods described herein.

In at least one embodiment, the computer-program product may be packaged in software. For example, the computer program product may be available (e.g., for sale, testing, etc.) on the Internet through an online platform (such as a university or hospital website). For example, the computer program product may be available for sale through an online commerce platform.

Further understanding of the subject matter of the present application can be obtained by reference to the following specific examples. These examples are non-limiting and are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

EXAMPLES

Example 1-Study #1

Methods:

The inventors retrospectively evaluated all EVLP cases from 2020-21 (n=113). Radiographs were scored by a thoracic radiologist blinded to donor lung outcome. Each ex vivo lung lobe was scored for five radiographic features (consolidation, infiltrates, atelectasis, nodules, and interstitial lines) on a scale of 0 to 3 by severity for a maximum radiographic lung score (RLS) of 18 per feature. The RLS was correlated with markers of lung injury (PaO2/FiO2 and edema) using Spearman's correlation.

Logistic regression was used to generate receiver operating curves (ROC) to derive the performance of RLS in predicting transplantation outcome following EVLP.

Results:

Consolidation and infiltrates after 1 h of EVLP were the most frequent findings (RLS 2.5±3.4 and 4.4±4.3). Interstitial lines were less frequent (RLS 1.76±3.53), with nodules and atelectasis being uncommon (RLS 0.60±1.30 and 0.41±0.65). At the first and third hours of perfusion, consolidation ($r=-0.536$ and $-0.608$, $p<0.0001$) and infiltrates ($r=-0.492$ and $-0.616$, $p<0.0001$) were inversely correlated with oxygenation (PaO2/FiO2), whereas interstitial lines were correlated with increased perfusate loss in the circuit reflecting increased edema ($r=0.244$, $p=0.019$, and $r=0.309$, $p=0.0047$). First-hour consolidation, infiltrates, atelectasis, nodules, and interstitial line RLS predicted the decision to transplant the lungs with ROC area of 87%, 88%, 52%, 58%, and 56%, respectively. First- and third-hour RLS from all five features predicted the decision to transplant with an area under the curve of 90% and 88%, respectively, and when combined, the value increased to 92%.

Conclusion:

Consolidation and infiltrates were the most frequent findings in lungs undergoing ex vivo lung perfusion. The Radiographic Lung Score (RLS) predicted the suitability of donor lungs for transplant. Radiographic ex vivo lung images provide key information for the clinical evaluation of donor lungs for transplantation.

Example 2-Study #2

Further details of Example 2 are provided below.

Methods

Study Group:

In this retrospective study, consecutive EVLP cases from Jan. 1, 2020, to May 14, 2021 were selected for analysis. Exclusion criteria included cases where the EVLP radiograph was missing, single lungs on circuit, cases where double lungs went to more than one recipient, cases of lobar transplantation, re-transplantation, and cases where clinical outcome information was absent. Retrospective EVLP data of the cases including baseline clinical characteristics and the decision to transplant were obtained from the Toronto Lung Transplant database.

Figure 1A:
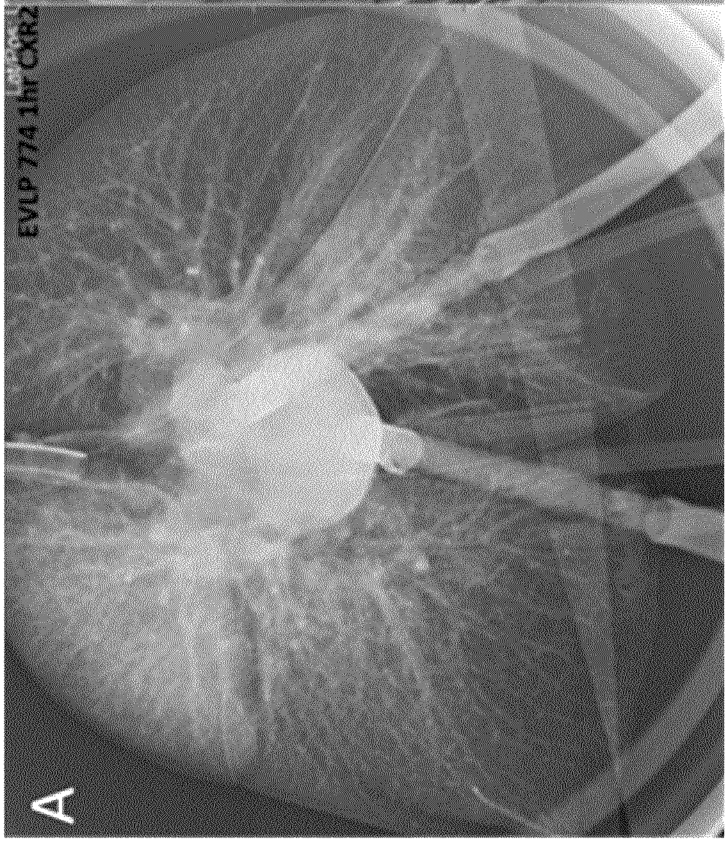

EVLP Procedure and Radiograph Acquisition:

The Toronto EVLP procedure was performed as previously described.[9] One hour and three hours after the initiation of EVLP, donor lungs were assessed in the EVLP basin using portable radiography (DRX-Revolution, Carestream Health, Rochester, New York, USA) by a medical radiation technologist. The radiographs were acquired from a source-to-image distance of around 100-125 cm directly above to cover the entire lungs with a voltage of 60 kVp and a current of 0.25 mAs, as shown in FIG. 1A. The corresponding donor lung photograph is shown in FIG. 1B. Donor lungs on the EVLP platform are not constricted by the rib cage and, when laid flat in the basin, result in an arched shape and the radiographs are similar to a lordotic projection. In clinical practice, the radiographs are then interpreted by the surgical team and stored on picture archiving and communications system. They are however not reported clinically by a radiologist.

Radiograph Analysis:

Radiographs were evaluated by a fellowship trained thoracic radiologist who was blinded to the donor lung outcome. In each radiograph, six lobes in donor lungs were identified: right upper lobe, right middle lobe, right lower lobe, left upper lobe, lingula, and left lower lobe. The radiologist scored each lobe for five radiologic abnormalities: consolidation, ground glass opacity (termed here as "infiltrates"), atelectasis, nodules, and interstitial lines utilizing established definitions for chest radiographs.[15] Each abnormality was scored from 0 to 3 for each lobe where 0 represents the absence of an abnormality, 1 the abnormality is occupying less than one third of the lobar volume ("mild"), 2 is occupying one-to two-thirds of the lobe ("moderate"), and 3 is more than two-thirds of the lobe involved ("severe"). The score for each radiographic abnormality (0-3) in each of the six lobes was summed for a maximum score of 18 for each radiographic finding, and this was termed the radiographic lung score (RLS).

Each radiograph was then scored for potential diagnoses present on a five-point Likert scale with 1 to 5 (1—the diagnosis is highly unlikely; 2 is unlikely; 3 is indeterminate; 4 is likely; and 5 is highly likely). The prespecified diagnoses were aspiration, pneumonia, contusion, and pulmonary edema. Finally, after interpreting the third-hour radiograph, the radiologist submitted an overall assessment of whether or not the lungs significantly improved, remained stable, or worsened compared to the first-hour radiograph based on expert opinion.

Clinical Outcome:

Donor lung physiological functions on EVLP were assessed using the edema and oxygenation parameters. The amount of circulating perfusate was recorded at the first and third hours of each EVLP case; decreased volume was likely due to perfusate accumulating in the donor lungs on EVLP, which was used as a surrogate measure for edema. The oxygenation index was measured by subtracting the pulmonary artery PO2 from the pulmonary vein PO2 in mmHg, using an FiO2 of 100%.

Clinical EVLP outcome was denoted by transplant outcome and duration of recipient mechanical ventilation. Transplant outcome was determined by the attending surgeon, often based on a holistic picture of donor lung functions and performance on EVLP such as oxygenation, radiographic appearance, perfusate loss, as well as other parameters like lung compliance and PH levels. Recipient outcome was indicated by the length of time that the recipient was intubated and ventilated. The threshold for high mechanical ventilation duration was set at three days, whereas those who spent less than three days mechanical ventilated was noted to have low mechanical ventilation days.

Figure 2:
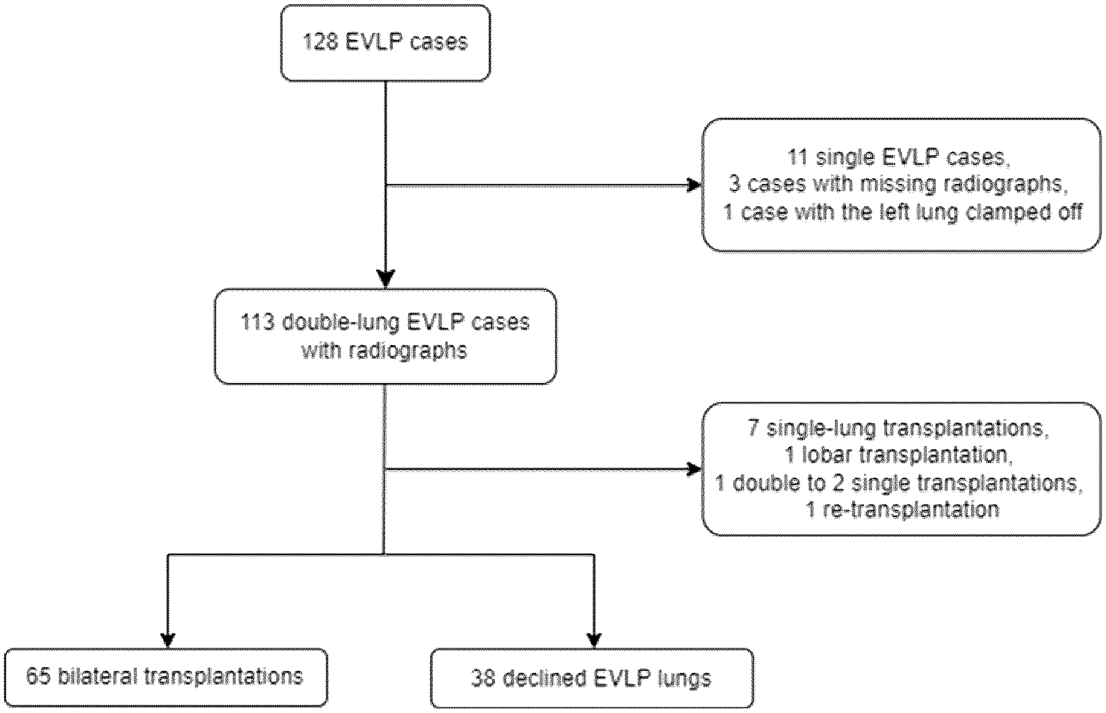
FIG. 2 is a schematic demonstrating patient selection including EVLP cases performed over January 2020 and May 2021, the number of EVLP cases, the exclusion criteria, and the donor lung outcomes following EVLP. EVLP-ex vivo lung perfusion.

Statistical Analysis:

Occurrences of each finding were described with means and standard deviations. Paired T-test was used to compare RLS from first-hour and third-hour images. Spearman correlations were conducted to associate the RLS with oxygenation and pulmonary edema, which was measured through perfusate lost during EVLP. Univariate regressions were performed using the RLS of each finding to predict the surgeon's decision to transplant. Five-fold cross-validation was run on multivariate regressions using oxygenation, edema, RLS by findings, and RLS by lung regions to predict the surgeon's decision to transplant as well as recipient outcome in terms of mechanical ventilation days. Elastic net was used with the lasso regularization set to 0.8 to reduce overfitting. In all regression analyses, EVLP cases with special outcomes (N=10) were excluded (as shown in FIG. 2), since these cases would affect recipient outcome. Statistical analysis was performed using John's Macintosh Project from Statistical Analysis System (JMP Software, Cary, NC) and Python (version 3.7). A threshold of $p<0.05$ was considered statistically significant.

Results

Donor Lung Characteristics:

There were 239 EVLP and lung transplantations performed from Jan. 1, 2020 to May 14, 2021. Of the 128 EVLP cases, 113 were included in the study following application of exclusion criteria, as shown in FIG. 2. Baseline donor lung characteristics for these cases are presented in Table 1.

TABLE 1

Baseline lung donor characteristics, physiologic measures on ex vivo lung perfusion, decision to transplant and early post-operative outcome.

| | n = 113 |
|---|---|
| **Donor characteristic** | |
| Mean age, years | 47.7 ± 15.8 |
| Male, n (%) | 64 (57) |
| Body mass index, kg/m$^2$ | 27.7 ± 6.3 |
| Cigarette use, n (%) | 61 (56) |
| **Cause of death, n (%)** | |
| Cardiac arrest | 55 (52) |
| Stroke | 31 (29) |
| Head trauma | 11 (10) |
| Other | 9 (8) |
| Donor last PaO2, (mmHg) | 372 ± 98 |
| **Donor lung physiology on EVLP** | |
| $\Delta PO_2$ | 419 ± 70 |
| Perfusate Loss | 202 ± 213 |
| **Donor lung outcome** | |
| Lungs transplanted, n (%) | 75 (66) |
| Intubation <72 hours, n (%) | 49 (65) |

The most common cause of donor death was cardiac arrest (n=55, 52%) at a mean age of 47.7±15.8 years, with 64 being male (57%). Most donor lungs were suitable for transplantation (n=75, 66%), and among the transplanted lungs, most of the lung transplant recipients were extubated in the first 72 hours post-transplantation (n=49, 65%).

Radiographic Lung Score (RLS)

Figure 3:
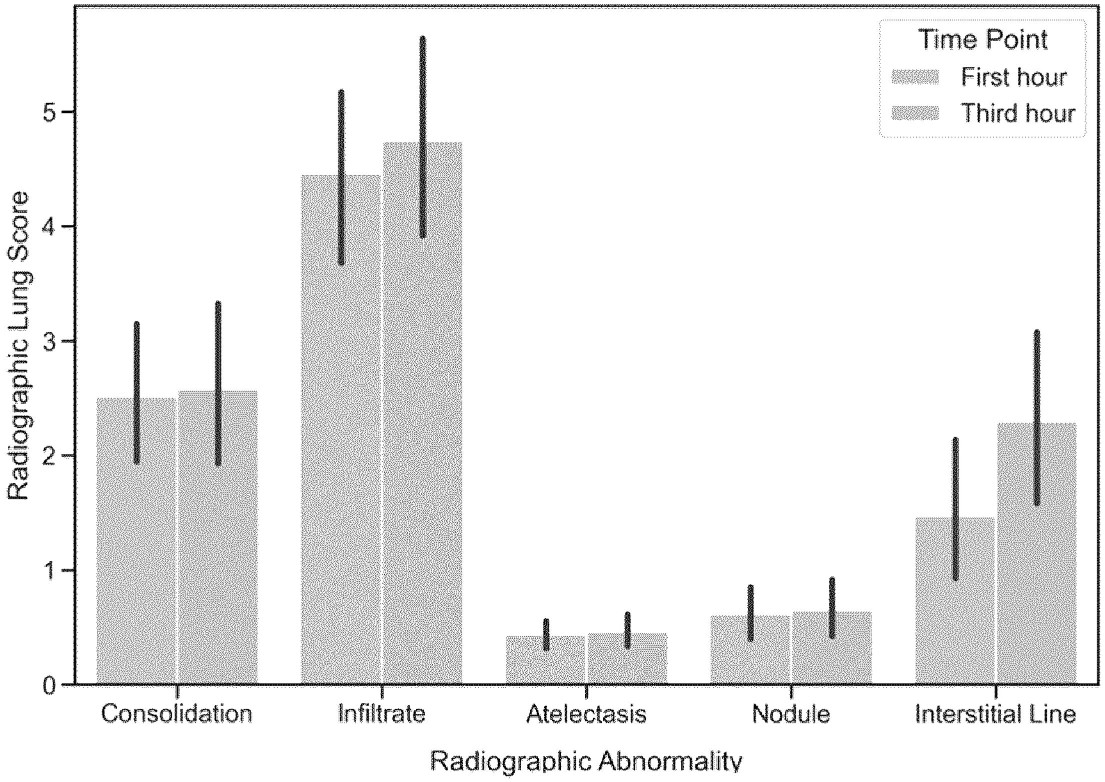
FIG. 3 is a graph showing mean and 95% confidence interval of radiographic lung scores per image for consolidation, infiltrate, atelectasis, nodule, and interstitial line at first (left bar) and third (right bar) hours of EVLP.
Figure 4A:
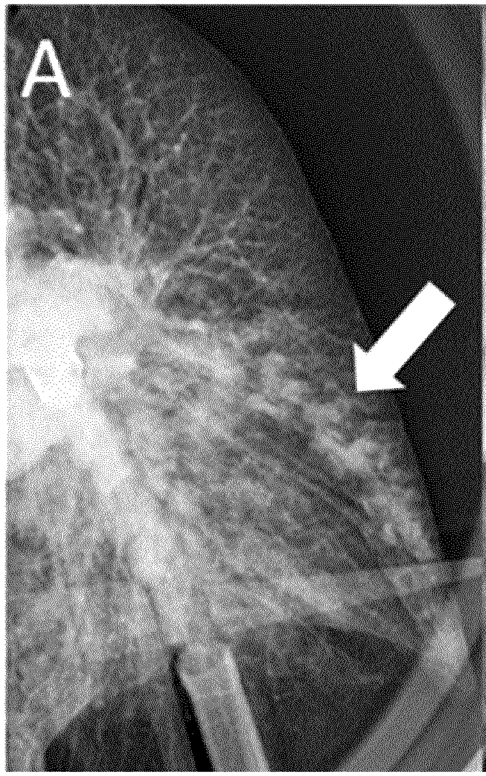
FIGS. 4A-4D are a series of images showing ex vivo lung perfusion (EVLP) radiograph at 1 hour (FIG. 4A) and three hours (FIG. 4B) demonstrating clustered nodule in the lingula (arrow) and a moderate amount of opacity in the left lower lobe that worsens on follow-up (*).
Figure 4B:
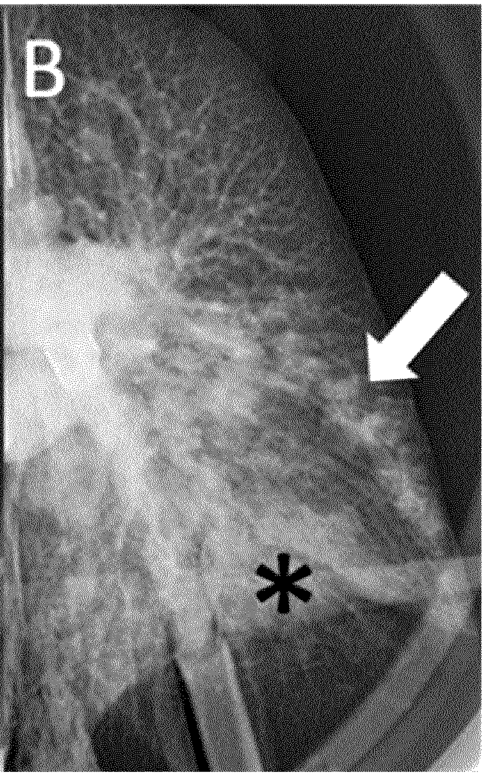
Figure 4C:
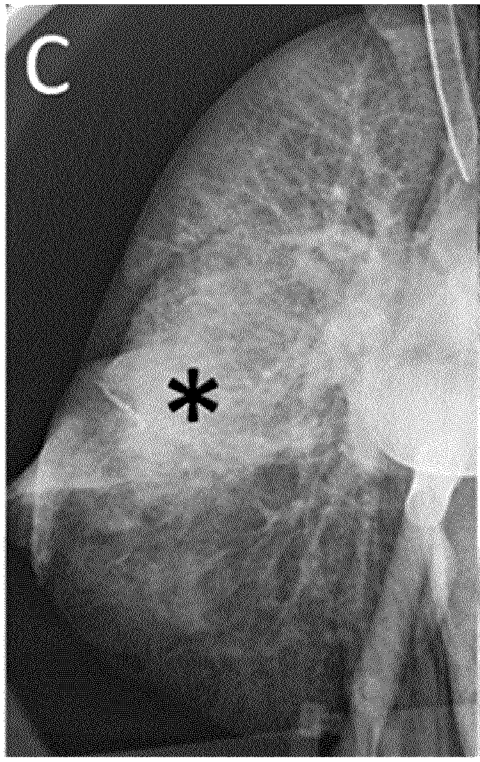
Figure 4D:
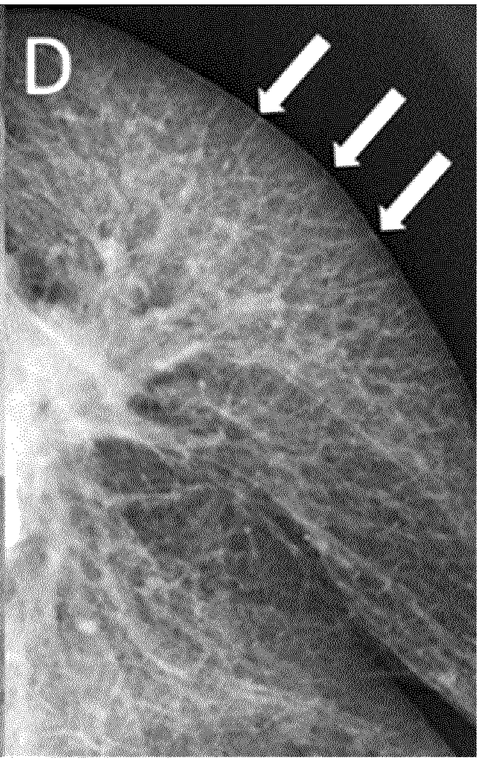

Consolidation and infiltrates were the most common findings and had a mean RLS of 2.6±3.3 and 4.6±4.3, respectively, over both time points, as shown in FIG. 3 with the findings at the first hour time point shown on the left and the findings at the third hour time point shown on the right. Atelectasis and nodules were uncommon with a lower mean RLS of 0.5±0.7 and 0.6±1.3, respectively. Examples of the radiographic findings are presented in FIGS. 4A-4D. The high standard deviations overall in the study show that the occurrence of abnormalities is case-dependent, and that there was a wide range of different donor lungs accepted and placed on EVLP.

Figure 5:
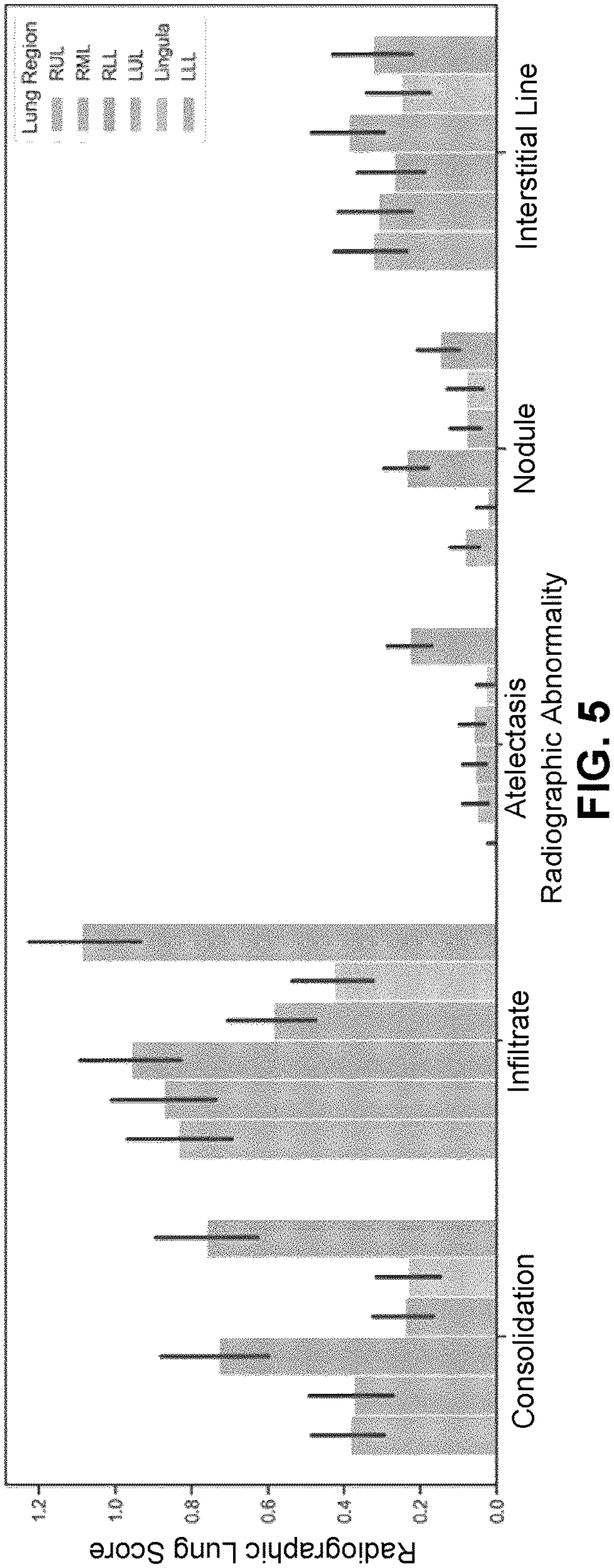
FIG. 5 is a graph showing the occurrence of radiographic abnormalities in different regions of donor lungs, indicated by mean radiographic lung scores and 95% confidence intervals of consolidation, infiltrate, atelectasis, nodule, and interstitial line for each of the following lung regions (from left to right bars): right upper lobe (RUL), right middle lobe (RML), right lower lobe (RLL), left upper lobe (LUL), lingula, and left lower lobe (LLL).

The occurrence frequency of radiographic abnormalities in different lobes of the lung is described in FIG. 5. There was a tendency for consolidation, infiltrates, and nodules to occur in the dependent lung (lowest portion of lung due to gravity) whereas interstitial lines tended to be diffuse. Atelectasis was especially common in the left lower lobe, presumably residual compressive atelectasis after removing the lung from the confines of the thorax and heart.

Consolidation ($p<0.001$) and infiltrate ($p<0.001$) scores were significantly lower in the first-hour radiographs of EVLP cases where radiographs from both time points were present (N=101), compared to those where EVLP was terminated before the second radiograph was taken (N=12).

Figure 7:
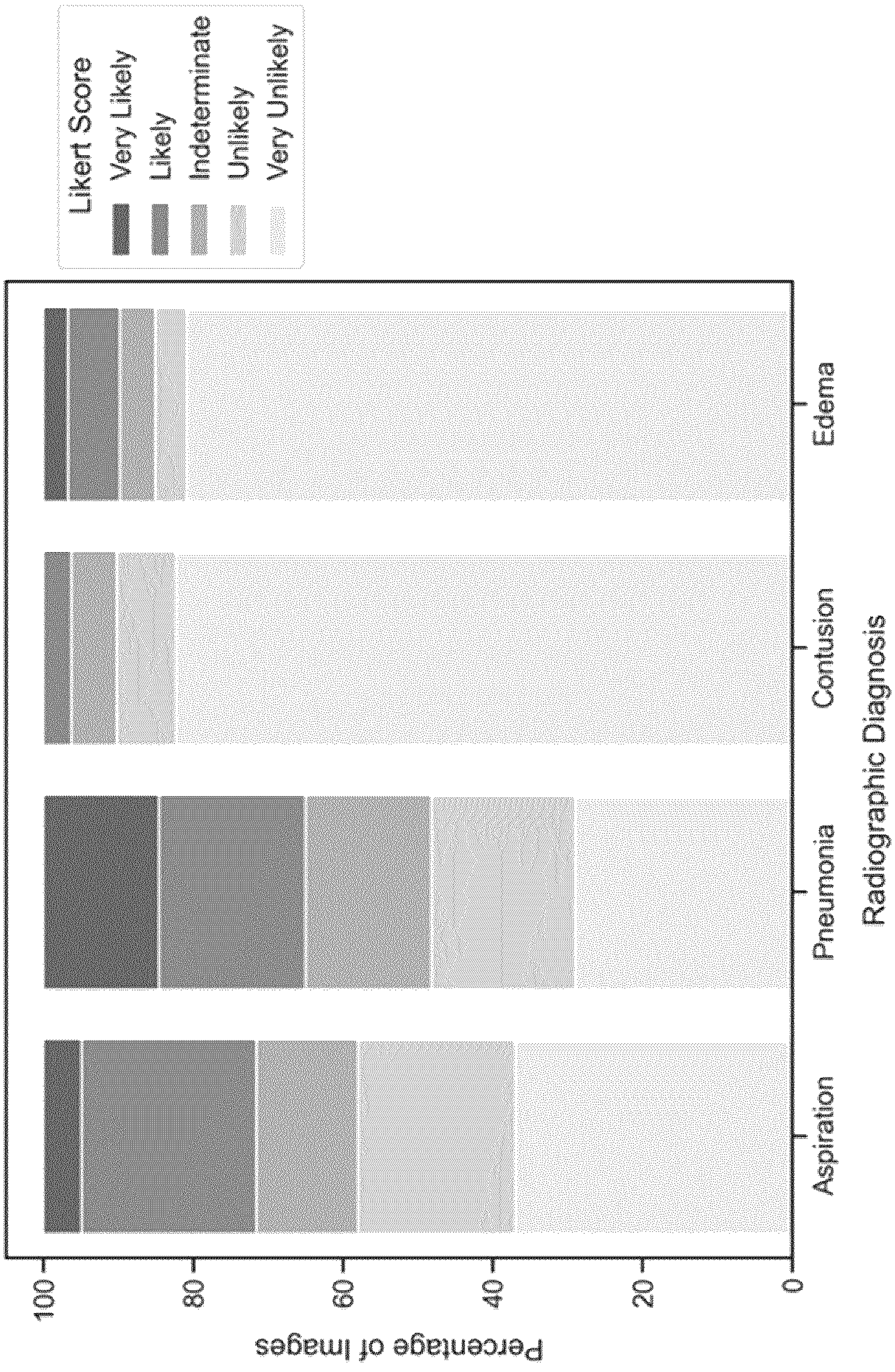
FIG. 7 is a graph showing Likert scores of one to five describing the likelihoods of radiographic diagnoses including aspiration, pneumonia, contusion, and edema in the radiographs.

FIG. 7 shows a stacked bar plot describing the likelihoods of aspiration, pneumonia, contusion, and edema across all images in this cohort. While aspiration and pneumonia had more evenly distributed scores, contusion and edema were predominantly unlikely.

Figure 6A:
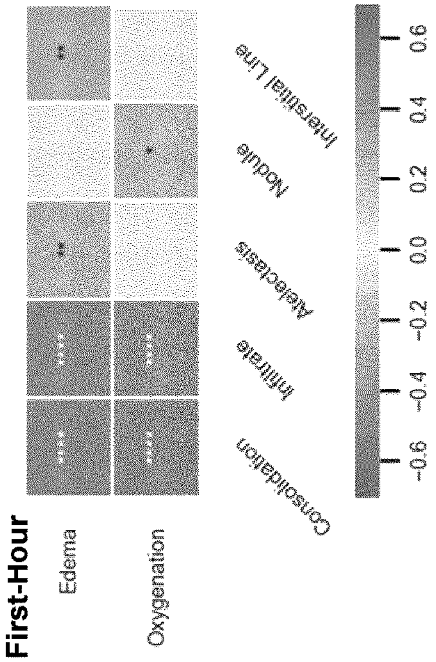
FIGS. 6A-6B are a series of heat maps correlating radiographic lung scores of consolidation, infiltrate, atelectasis, nodule, and interstitial line to ΔPO2 and perfusate lost after the first hour (FIG. 6A) and the third hour (FIG. 6B) of EVLP (Spearman correlations, *$p<0.05$,  $p<0.01$, * $p<0.001$, **** $p<0.0001$).
Figure 6B:
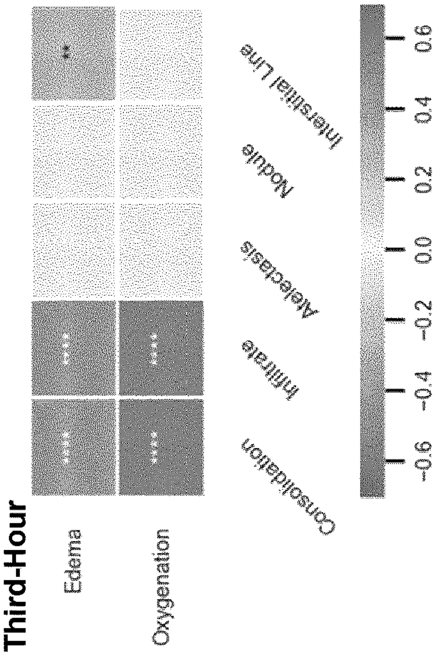

Donor Lung Physiology:

Donor lung radiographic abnormalities were then correlated with lung performance on EVLP, as shown in FIGS. 6A-6B. The ΔPO2 at first and third hours in the current EVLP cohort ranged from 205 to 547 mmHg, while the perfusate lost during EVLP ranged from 0 to 1100 mL. Consolidation and infiltrate RLS at first and third hours were significantly associated with lower ΔPO2 and higher volumes of perfusate lost (absolute Spearman coefficients of 0.42 to 0.58, $p<0.0001$). Interstitial lines at first ($r=0.30$, $p=0.0025$) and third ($r=0.27$, $p=0.0091$) hour of EVLP were associated with more severe edema. Nodules and atelectasis at first hour of EVLP were inversely correlated with ΔPO2 ($r=-0.24$, $p=0.011$) and enhanced edema ($r=0.27$, $p=0.007$), respectively.

Decision to Transplant:

Similar to results from the correlation analysis, consolidation and infiltrates appeared to perform best in logistic regression predicting the decision to transplant. First-hour RLS of consolidation, infiltrates, atelectasis, nodules, and interstitial lines returned an area under the receiver operating characteristic (AUROC) curve of 0.87, 0.88, 0.52, 0.58, and 0.56, respectively. Third-hour RLS of the same abnormalities had a similar AUROC of 0.86, 0.87, 0.54, 0.56, 0.59, respectively.

Figure 8:
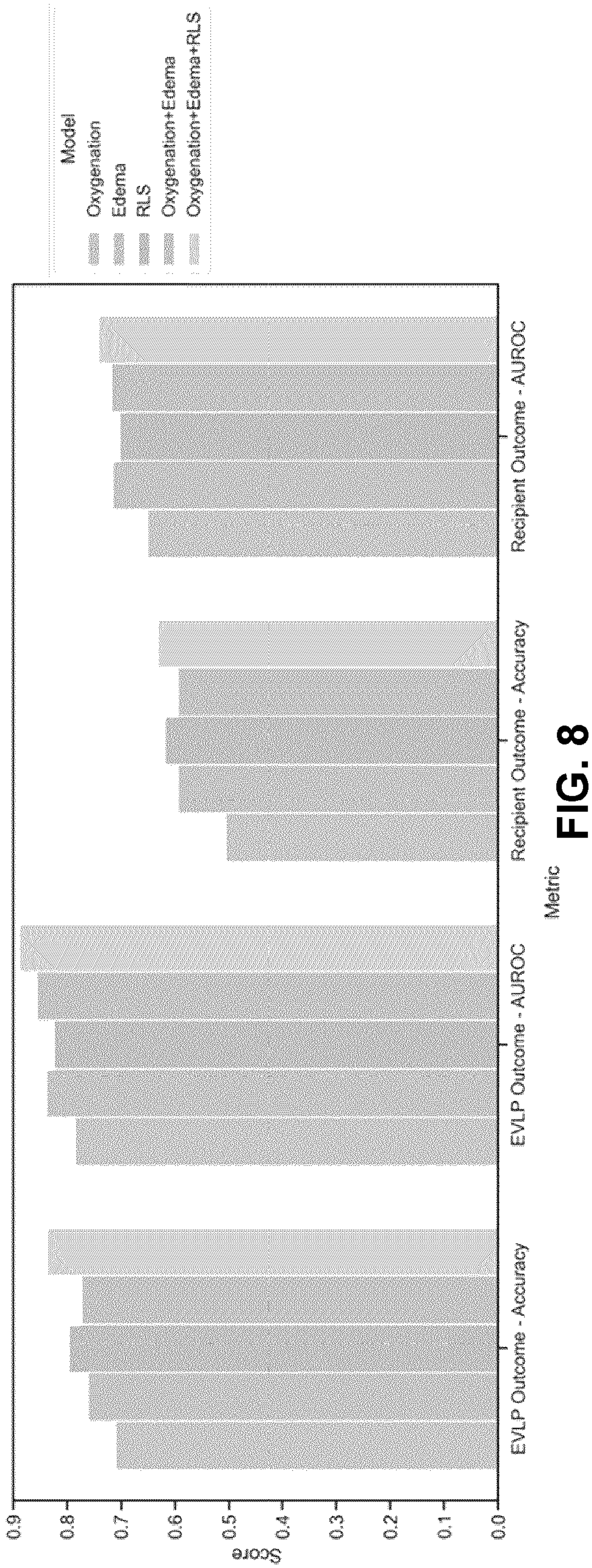
FIG. 8 is a graph showing multivariate regression cross-validation results for EVLP outcome and recipient outcome in accuracy and AUROC. Bar colours represent models with different combinations of oxygenation, edema, and radiographic lung score (RLS) as inputs (from left to right bards: 1) oxygenation, 2) edema, 3) RLS, 4) oxygenation and edema and 5) oxygenation, edema and RLS).
Figure 9A:
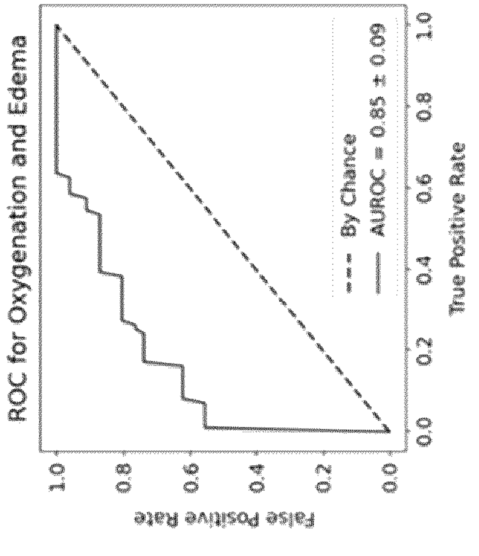
FIGS. 9A, 9B and 9C are graphs showing receiver operating characteristic (ROC) curves of multivariate regression models to classify for declined donor lungs using edema and oxygenation (FIG. 9A), RLS (FIG. 9B), and edema, oxygenation, and RLS (FIG. 9C) as inputs.
Figure 9B:
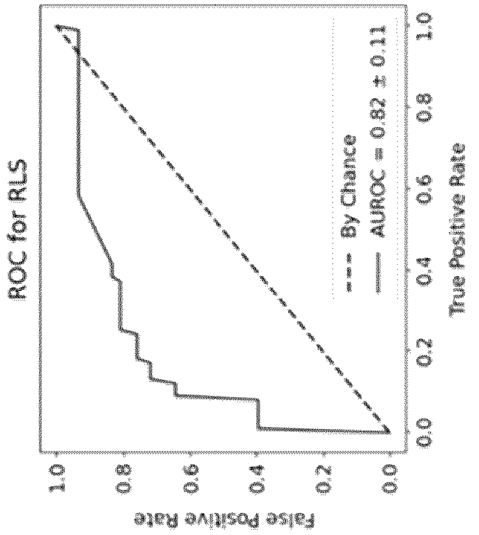
Figure 9C:
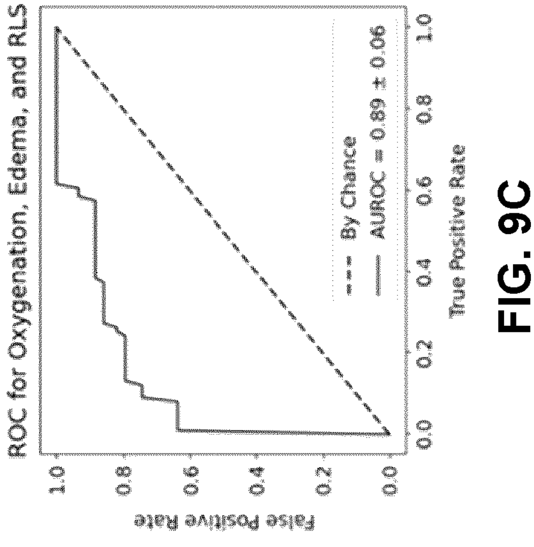

Cross-validation results of the multivariate regression (as shown in FIG. 8) show that the conventional physiologic measures of edema and oxygenation at both time points predicted the declined lungs with accuracies of 0.76 and 0.71 and AUROCs of 0.84 and 0.79, respectively. RLS at both time points performed well during cross validation when predicting for declined lungs (accuracy=0.80, AUROC=0.82) and recipient outcomes (accuracy=0.62, AUROC=0.70). When added on top of the existing edema and oxygenation metrics, RLS improved the overall accuracy and AUROC (FIG. 8); the ROC curves of edema, oxygenation, and RLS regression models for decision to transplant are shown in FIGS. 9A, 9B and 9C. The final accuracy and AUROC were 0.84 and 0.89 when predicting for declined lungs, and 0.63 and 0.74 when predicting for mechanical ventilation outcomes.

DISCUSSION

In the EVLP donor lung radiographs from the cohort of 113 EVLP cases analyzed, consolidation and infiltrates were more prevalent. High consolidation and infiltrate scores correlated significantly with reduced lung oxygenation and increased pulmonary edema; they additionally performed better than atelectasis, nodules, and interstitial lines at predicting surgeon's decision to transplant.

Compared to the conventional edema and oxygenation metrics, the radiographic findings performed well in multivariate regression when classifying transplanted versus declined donor lungs as well as recipient mechanical ventilation outcomes. Adding RLS to the model with the existing edema and oxygenation features improved the prediction accuracy and AUROC, while providing a more comprehensive way of evaluating donor lungs. As opposed to edema and oxygenation, which were represented by single numbers-amount of perfusate lost and ΔPO2, RLS shows a variety of findings as appeared under X-ray, the severity, as well as the regional heterogeneity of abnormality.

Figure 11A:
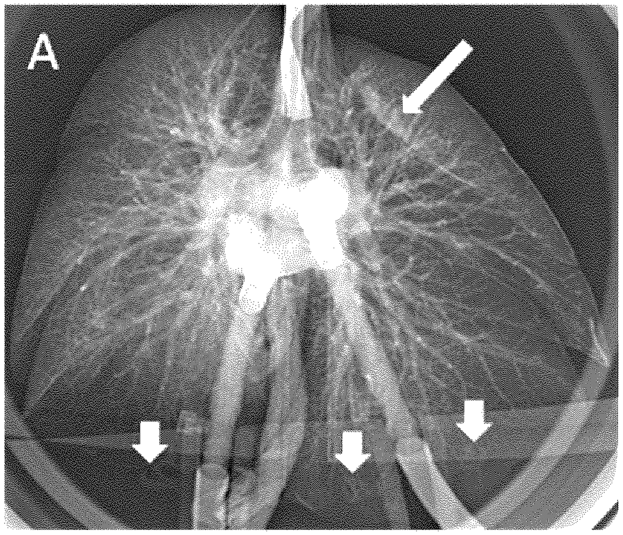
FIGS. 11A-11B show an example of the artifacts present in EVLP radiographs.
Figure 11B:
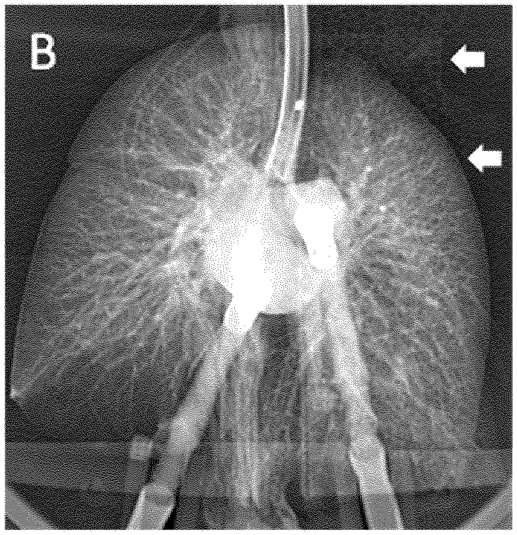

Without wishing to be bound to this theory, the results yielded important observations in the radiograph acquisition technique for implementation going forward. The first is the imaging of the entire lung, ideally in a single EVLP image, which can be a challenge given the height of the EVLP basin containing the lung relative to the X-ray source. The second observation is the position of venous and arterial cannulas that frequently obscured portions of the lung, often the lower lobes where abnormalities were most frequently observed. The final observation were occasional artifacts, often caused by sponges within the basin that could mimic pathology when overlying the lung (FIGS. 11A-11B).

Radiographic assessments are usually performed pre- and post-transplantation at the donor hospital and during recipient follow-up; they are currently not part of the EVLP procedure in most transplant centres. Therefore, to the inventors' knowledge, this is the first study to systematically analyze large-scale EVLP radiographs.[4, 14, 16-19] Integrating radiographic assessments during EVLP may provide physicians a unique opportunity to visualize the internal structure and potential damages of donor lungs, allowing for more informed diagnosis and targeted treatment.

Example 3-Study #3

A study was performed to determine whether certain radiographic features can be used to predict transplantation outcomes using regression. In particular, the study was performed to determine whether the cut-off values for the radiographic features mentioned earlier in the description can have predictive power. For example, for certain cut-off levels for certain radiographic features labeled by a radiologist on an arbitrary scale (i.e., 0-3), the sensitivity and specificity of prediction transplant decisions can be determined. For example, for the consolidation radiographic feature, the sensitivity and specificity were determined to be 66% and 94%, respectively.

Methods:

RLS scores for all five radiographic features were used to predict outcomes (i.e., transplant vs. declined lungs) using trained regression and decision tree models, and then assessed by AUROC. From this analysis, a cut-off levels for the different radiographic features may be determined using mathematical approaches (i.e., Youden's J) and the resulting sensitivity, and specificity of the RLS at this cut-off level can be determined.

Results:

Example results are shown for the radiographic features of consolidation and infiltrate in Table 2. Declined lungs had a higher first-hour consolidation RLS (5.5 vs 0.92, p<0.0001) and infiltrate RLS (8.1 vs 2.6, p<0.0001) than transplanted lungs. It is noted that the RLS thresholds defined by Youden's J separated the mean RLS of declined lungs from the mean RLS of transplanted lungs shown in the first two columns.

TABLE 2

AUC table of sensitivity, specificity, Youden's J for Radiographic features consolidation and infiltrate

| | Declined Lung RLS | Transplanted Lung RLS | Youden's J | Sensitivity | Specificity |
|---|---|---|---|---|---|
| Consolidation | 5.5 | 0.92 | RLS = 4 | 66% | 94% |
| Infiltrate | 8.1 | 2.6 | RLS = 6 | 76% | 89% |

Using Machine Learning:

This study also investigated whether radiographic features that make up the radiographic lung score (i.e., from manual labels provided by radiologists) can be used in a machine learning model such as, but not limited to, the XGBoost model, for example, to predict transplant outcomes.

Methods:

The XGBoost model described in the Applicant's co-pending PCT patent application entitled "SYSTEMS AND METHODS FOR PREDICTING OUTCOMES FOR A LUNG UNDERGOING AN EX VIVO LUNG PERFUSION", was used in this study. The input features to the model are the same as the radiographic features described in the linear regression analysis and in accordance with the description herein (i.e., manual labels provided by radiologists). The predicted outcomes were selected to be transplanted with extubation +/−72 h and lungs unsuitable for transplantation (e.g., three groups). This study included N=102 EVLP cases. The mean age and BMI of study participants are 47.7 and 27.5, respectively, with 57% being male and 47% being DBD donors.

Results:

The results are shown in Table 3 which shows the XGBoost model performance assessed by AUROC for different combinations of input features. The test results in predicting post-transplant outcomes using RLS and/or InsighTx features. The AUROC for the model when only radiographic features were used as input was 77.3%+/−1.4%. The AUROC for the model when only InsighTx features were used as input was 79.1%+/−2.2%. The AUROC for the model when both the radiographic features and InsighTx features were used was 80.2%+/−2.0%.

Figure 12:
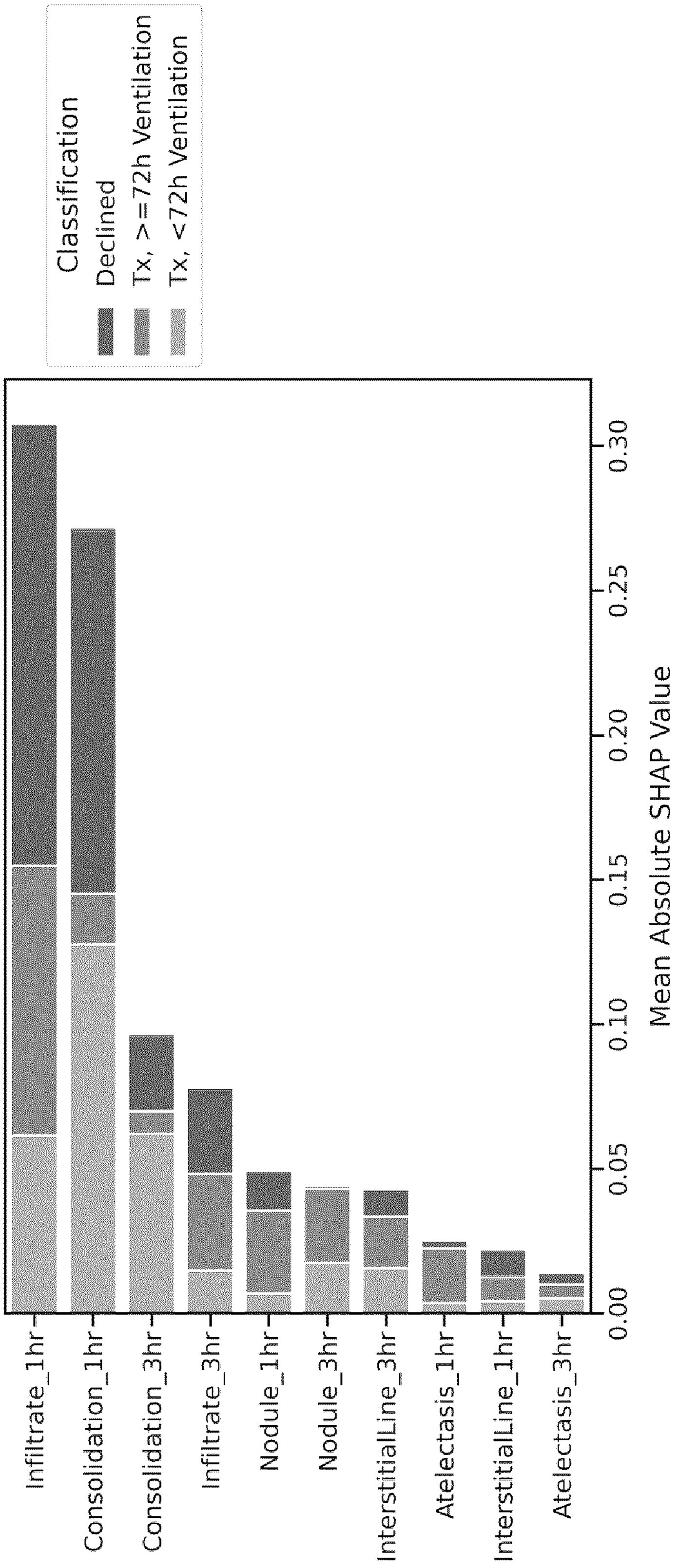
FIG. 12 shows the relative importance of different radiographic features that were input to a machine learning model as determined using SHAP (Shapley Additive Explanations).

Referring now to FIG. 12, the relative feature importance values when radiographic features were used as input to the XGBoost model can be determined using SHAP (Shapley Additive Explanations). FIG. 12 shows that the presence of infiltrates in the first hour are the most important feature followed by consolidation at 1 h, etc. Infiltrate and consolidation appear to be very informative radiographic features when it comes to outcome classification, and first-hour infiltrate and consolidation RLS appear to be more predictive than third-hour infiltrate and consolidation RLS. Relative feature importance values for the XGBoost model based on radiographic (RLS) features to predict unsuitable donor lungs (class 2), transplanted lungs and recipient extubation in less than 72 h (class 0) or greater than 72 h (class 1).

TABLE 3

XGBoost model performance in AUROC predicting post-transplant outcomes using RLS and InsighTx features.

| | Only RLS | Only InsighTx Features | RLS + InsighTx Features | p value |
|---|---|---|---|---|
| Test Set AUROC (%) | 77.3 ± 1.4% | 79.1 ± 2.2% | 80.2 ± 2.0% | $p = 0.032$*<br>$p < 0.0001$** |

*p value comparing model with all features and model with just InsighTx features
**p value comparing model with all features and model with just radiological features Assessing Adding Radiographic Features to Machine Learning Models (InsighTx) to Enhance Model Performance:

The study data was used to determine whether adding radiographic features (i.e., RLS) to all of the other EVLP assessments (i.e., InsighTx model and other input features described in the Applicant's co-pending PCT patent application "SYSTEMS AND METHODS FOR PREDICTING OUTCOMES FOR A LUNG UNDERGOING AN EX VIVO LUNG PERFUSION") might improve donor lung outcome prediction.

Method:

The same XGBoost model described previously was provided with input features including the radiographic features scored as described herein and all the other EVLP assessment features (i.e., physiological, biochemical, donor, recipient, etc.) as described in the above-noted Applicant's co-pending PCT patent application. The predicted outcomes are the same as previously described: transplanted with extubation +/−72 h and lungs unsuitable for 3 classes.

Results:

Table 5 shows the relative feature importance of the Xray and InsighTx model. The analysis shows that Xray features (i.e., radiographic features) are highly-ranked in terms of importance. Since small dataset was used, it is possible for this ranking to change with more data, but the analysis shows that a machine learning model using InsighTx and radiographic input features performs better and that radiographic features appear to provide useful information for determining outcome predictions.

TABLE 5

Top ten ranked radiographic and EVLP features in the XGBoost model by endpoint

| | Overall Model Performance | Extubated <72 h Post-Transplant | Extubated >72 h Post-Transplant | Unsuitable for Transplant |
|---|---|---|---|---|
| 1 | Radiographic Infiltrate | Radiographic Infiltrate | $\Delta pCO_2$ | Radiographic Infiltrate |
| 2 | Edema | Perfusate Exchange Volume | Dynamic Compliance | Edema |
| 3 | Perfusate Exchange Volume | Edema | $\Delta pO_2$ | Perfusate Exchange Volume |
| 4 | Dynamic Compliance | Pulmonary Vascular Resistance | Edema | Static Compliance |
| 5 | Static Compliance | pH | Static Compliance | Lactate |
| 6 | Radiographic Consolidation | Radiographic Consolidation | pH | Radiographic Consolidation |
| 7 | Pulmonary Vascular Resistance | $HCO_3$ | Base Excess | Dynamic Compliance |
| 8 | pH | $K^+$ | Perfusate Exchange Volume | pH |
| 9 | $\Delta pO_2$ | $Ca^{2+}$ | LA Pressure | Pulmonary Vascular Resistance |
| 10 | Lactate | Dynamic Compliance | $K^+$ | $\Delta pO_2$ |

Computer vision (deep neural networks) to predict donor lung outcomes:

The radiographic features that are identified manually require review by a trained radiologist) are scored on an arbitrary scale (0-3) to generate the RLS for a radiographic feature. In this part of the study computer vision (e.g., deep learning AI) were also used to process the images. For example, clinical EVLP X-ray images were labelled based on donor lung outcome (i.e., unsuitable, transplant with extubation +/−72 h) and a computational approach (e.g., a deep learning AI model) was used to find patterns in the images that were associated with the outcomes. This data demonstrates that a trained radiologist is not needed to analyze the X-rays to provide labelled X-ray images or RLS scores since a deep learning AI model, may provide this functionality.

Methods:

Different deep learning model architectures were tested including: ResNet-50, ResNext-50, RexNet-100, DenseNet-121, EfficientNet-B2, EfficientNet-B3, which are examples of convolution neural networks (CNNs). All models were pre-trained using the ImageNet dataset (~1,000,000 natural images) or the NIH CADLab (subset of ~11,000 images). The dataset was split 80:20 for training and testing respectively. The neural network models were trained to predict: (i) EVLP outcome (i.e., transplant yes or no (n=1017, two groups) (Table 6)) or (ii) donor lung outcome (transplanted with extubation <72 h, more than >72 h, or declined for transplant (n=993, three groups) (Table 7))

Results:

The NIH-pretrained results are based on training the deep learning models on chest X-ray images from the NIH public dataset. The CADLab-pretrained results are models pre-trained using a subset of the NIH data, which contains labels that are less ambiguous as they involve human validation. The baseline models are implemented without any pretraining (without the use of NIH or CADLab data). In the baseline models, neural networks are trained directly on the EVLP task (e.g., outcome classification). The same trends are seen in the results of both Tables 6 and 7. The inventors further believe that deep learning models can be applied to not only radiographic input features but all other EVLP data features (i.e., InsightTx, kinetic, donor, and recipient features) to further improve performance.

TABLE 6

AUROCs using CNNs to classify transplant decisions in EVLP X-ray images

| | Baseline (no pretraining) | NIH-pretrained | CADLab-pretrained |
|---|---|---|---|
| ResNet-50 | 74.6 | 86.4 | 86.4 |
| ResNeXt-50 | 71.0 | 84.9 | 85.6 |
| RexNet-100 | 74.5 | — | 88.1 |
| EfficientNet-B2 | 71.7 | 84.6 | 84.8 |
| EfficientNet-B3 | 69.9 | 88.5 | 86.0 |
| DenseNet-121 | 73.7 | 84.9 | 84.3 |

TABLE 7

AUROCs using CNNs to classify donor lung outcomes in EVLP X-ray images

| | Baseline (no pretraining) | NIH-pretrained | CADLab-pretrained |
|---|---|---|---|
| ResNet-50 | 65.0 | 74.8 | 71.1 |
| ResNeXt-50 | 65.6 | 70.8 | 73.7 |
| RexNet-100 | 68.2 | 69.7 | 73.1 |
| EfficientNet-B2 | 67.6 | 74.0 | 79.4 |
| EfficientNet-B3 | 69.3 | 73.6 | 71.4 |
| DenseNet-121 | 65.0 | 75.5 | 71.7 |

While the applicant's teachings described herein are in conjunction with various embodiments for illustrative purposes, it is not intended that the applicant's teachings be limited to such embodiments. On the contrary, the embodiments of the present disclosure described above are intended to be examples only and it is not intended that the applicant's teachings be limited to such embodiments. The present disclosure may be embodied in other specific forms. Alterations, modifications, and variations to the disclosure may be made without departing from the intended scope of the present disclosure. While the systems, devices, and processes disclosed and shown herein may comprise a specific number of elements/components/steps, the systems, devices, and processes may be modified to include additional or fewer of such elements/components or steps. For example, while any of the elements/components/steps disclosed may be referenced as being singular, the embodiments disclosed herein may be modified to include a plurality of such elements/components. Selected features from one or more of the example embodiments described herein in accordance with the teachings herein may be combined to create alternative embodiments that are operable and have utility but are not explicitly described. All values and sub-ranges within disclosed ranges are also disclosed. The subject matter described herein intends to cover and embrace all suitable changes in technology. The entire disclosures of all references recited above are incorporated herein by reference.

CITATIONS FOR REFERENCES REFERRED TO IN THE SPECIFICATION

1. Khush K K, Hsich E, Potena L, et al. The International Thoracic Organ Transplant Registry of the International Society for Heart and Lung Transplantation: Thirty-eighth adult heart transplantation report-2021; Focus on recipient characteristics. J Heart Lung Transplant. 2021.
2. Valapour M, Lehr C J, Skeans M A, et al. OPTN/SRTR 2018 Annual Data Report: Lung. Am J Transplant. 2020; 20 Suppl s1: 427-508.
3. Sadaria M R, Smith P D, Fullerton D A, et al. Cytokine Expression Profile in Human Lungs Undergoing Normothermic Ex-Vivo Lung Perfusion. The Annals of Thoracic Surgery. 2011; 92 (2): 478-484. doi: 10.1016/j.athoracsur.2011.04.027.
4. Cypel M, Yeung J C, Machuca T, et al. Experience with the first 50 ex vivo lung perfusions in clinical transplantation. The Journal of Thoracic and Cardiovascular Surgery. 2012; 144 (5): 1200-1207. doi: 10.1016/j.jtcvs.2012.08.009.
5. Cypel M, Keshavjee S. Extracorporeal lung perfusion (ex-vivo lung perfusion): Current Opinion in Organ Transplantation. 2016; 21 (3): 329-335. doi: 10.1097/MOT.0000000000000320.
6. Yeung J C, Cypel M, Keshavjee S. Ex-vivo lung perfusion: the model for the organ reconditioning hub. Current Opinion in Organ Transplantation. 2017;22 (3): 287-289. doi: 10.1097/MOT.0000000000000404.
7. Weathington N M, Álvarez D, Sembrat J, et al. Ex vivo lung perfusion as a human platform for preclinical small molecule testing. JCI Insight. 2018; 3 (19): e95515. doi: 10.1172/jci.insight.95515.
8. Cypel M, Yeung J C, Donahoe L, et al. Normothermic ex vivo lung perfusion: Does the indication impact organ utilization and patient outcomes after transplantation? The Journal of Thoracic and Cardiovascular Surgery. 2020; 159 (1): 346-355.e1. doi: 10.1016/j.jtcvs.2019.06.123.
9. Cypel M, Yeung J C, Hirayama S, et al. Technique for prolonged normothermic ex vivo lung perfusion. J Heart Lung Transplant. 2008; 27:1319-25.
10. Murala J S, Whited W M, Banga A, et al. Ex vivo lung perfusion: how we do it. Indian J Thorac Cardiovasc Surg. 2021:1-12.
11. Sage A T, Richard-Greenblatt M, Zhong K, et al. Prediction of donor related lung injury in clinical lung transplantation using a validated ex vivo lung perfusion inflammation score. J Heart Lung Transplant. 2021; 40:687-95.
12. Cypel M, Yeung J C, Liu M, et al. Normothermic ex vivo lung perfusion in clinical lung transplantation. N Engl J Med. 2011; 364:1431-40.
13. Yeung J C, Krueger T, Yasufuku K, et al. Outcomes after transplantation of lungs preserved for more than 12 h: a retrospective study. The Lancet Respiratory Medicine. 2017;5 (2): 119-124. doi: 10.1016/S2213-2600 (16) 30323-X.
14. Machuca T N, Mercier O, Collaud S, et al. Lung Transplantation With Donation After Circulatory Determination of Death Donors and the Impact of Ex Vivo Lung Perfusion: DCDD Lung Transplantation and EVLP.

American Journal of Transplantation. 2015; 15 (4): 993-1002. doi: 10.1111/ajt. 13124.
15. Hansell D M, Bankier A A, MacMahon H, McLoud T C, Muller N L and Remy J. Fleischner Society: glossary of terms for thoracic imaging. Radiology. 2008; 246:697-722.
16. Tian D, Wang Y, Shiiya H, et al. Outcomes of marginal donors for lung transplantation after ex vivo lung perfusion: A systematic review and meta-analysis. The Journal of Thoracic and Cardiovascular Surgery. 2020; 159 (2): 720-730.e6. doi: 10.1016/j.jtcvs.2019.07.087.
17. Egan T M, Haithcock J A, Nicotra W A, et al. Ex Vivo Evaluation of Human Lungs for Transplant Suitability. The Annals of Thoracic Surgery. 2006;81 (4): 1205-1213. doi: 10.1016/j.athoracsur.2005.09.034.
18. Fisher A, Andreasson A, Chrysos A, et al. An observational study of Donor Ex Vivo Lung Perfusion in UK lung transplantation: DEVELOP-UK. Health Technol Assess. 2016; 20 (85): 1-276. doi: 10.3310/hta20850.
19. Wallinder A, Ricksten S E, Hansson C, et al. Transplantation of initially rejected donor lungs after ex vivo lung perfusion. The Journal of Thoracic and Cardiovascular Surgery. 2012; 144 (5): 1222-1228. doi: 10.1016/j.jtcvs.2012.08.011.

The invention claimed is:

1. A method for predicting transplant suitability of an ex vivo donor lung and/or patient outcome following transplant of the donor lung, comprising:

measuring in a radiograph of the donor lung at least two radiographic features in a plurality of lobes of the donor lung, the radiographic features optionally selected from consolidation, infiltrate, atelectasis, nodule and interstitial line, and the plurality of lobes selected from right upper lobe, right middle lobe, right lower lobe, left upper lobe, lingula and left lower lobe;

determining in each of the lobes of the plurality of lobes a lobar score for each of the radiographic features measured;

combining the lobar score of each of the lobes of the plurality of lobes to generate a radiograph lung score for each of the radiographic features measured;

comparing the radiograph lung score with a control radiograph lung score or a cut-off level for a corresponding radiographic feature; and predicting the transplant suitability of the donor lung and/or patient outcome following transplant of the donor lung based on the comparison of the radiograph lung score with the control radiograph lung score or cut-of level, optionally based on differences or similarities between the radiograph lung score and the control radiograph lung score or cut-off level.

2. The method of claim 1, wherein each of the radiographic features measured in each of the lobes of the plurality of lobes is attributed a score of 0, 1, 2 or 3, with 0 indicating an absence of the radiographic feature, 1 indicating a mild level of the radiographic feature, 2 indicating a moderate level of the radiographic feature and 3 indicating a severe level of the radiographic feature.

3. The method of claim 2, wherein the score of 1 indicates the radiographic feature occupies less than one third of the lobar volume, the score of 2 indicates the radiographic feature occupies one third to two thirds of the lobar volume and the score of 3 indicates the radiographic feature occupies more than two thirds of the lobar volume.

4. The method of claim 1, wherein (a) the radiographic features comprise consolidation and infiltrate, (b) the radiographic features comprise consolidation, infiltrate and interstitial line or (c) the radiographic features are consolidation, infiltrate, atelectasis, nodule and interstitial line.

5. The method of claim 1, wherein the patient outcome is selected from number of days of mechanical ventilation, ICU length of stay, hospital length of stay, APACHE score and post graft dysfunction (PGD) grade, optionally PGD0/1, PGD2 or PGD3.

6. The method of claim 1, wherein the method comprises measuring the radiographic features in at least 3, at least 4 or at least 5 lobes.

7. The method of claim 1, wherein the method comprises measuring the radiographic feature of consolidation in the 6 lobes, wherein the radiograph lung score for consolidation of less than 8, less than 7, less than 6, less than 5, less than 4 or less than 3 is indicative the donor lung is likely suitable for transplant and/or the patient is likely to have a good outcome following transplant;

wherein the method comprises measuring the radiographic feature of infiltrate in the 6 lobes, wherein the radiograph lung score for infiltrate of less than 8, less than 7, less than 6, less than 5, less than 4 or less than 3 is indicative the donor lung is likely suitable for transplant and/or the patient is likely to have a good outcome following transplant;

wherein the method comprises measuring the radiographic feature of atelectasis in the 6 lobes, wherein the radiograph lung score for atelectasis of less than 2, less than 1.5, less than 1 or less than 0.5 is indicative the donor lung is likely suitable for transplant and/or the patient is likely to have a good outcome following transplant;

wherein the method comprises measuring the radiographic feature of nodule in the 6 lobes, wherein the radiograph lung score for nodule of less than 2, less than 1.5, less than 1 or less than 0.75 is indicative the donor lung is likely suitable for transplant and/or the patient is likely to have a good outcome following transplant;

wherein the method comprises measuring the radiographic feature of interstitial line in the 6 lobes, wherein the radiograph lung score for interstitial line of less than 6, less than 5, less than 4 or less than 3 is indicative the donor lung is likely suitable for transplant and/or the patient is likely to have a good outcome following transplant; and/or wherein the good outcome following transplant comprises three days or less of mechanical ventilation and/or being free from a graft-related death causes within 30 days, primary graft dysfunction grade 3 (PGD3), extracorporeal life support, extracorporeal membrane oxygenation and/or prolonged hospital/ICU stays.

8. The method of claim 1, wherein the method comprises measuring the radiographic feature of consolidation in the 6 lobes, wherein the radiograph lung score for consolidation of greater than 8, greater than 9, greater than 10 or greater than 11 is indicative the donor lung is likely not suitable for transplant and/or the patient is likely to have a poor outcome following transplant;

wherein the method comprises measuring the radiographic feature of infiltrate in the 6 lobes, wherein the radiograph lung score for infiltrate of greater than 8, greater than 9, greater than 10 or greater than 11 is indicative the donor lung is likely not suitable for transplant and/or the patient is likely to have a poor outcome following transplant;

wherein the method comprises measuring the radiographic feature of atelectasis in the 6 lobes, wherein the radiograph lung score for atelectasis of greater than 2, greater than 3, greater than 4 or greater than 5 is indicative the donor lung is likely not suitable for transplant and/or the patient is likely to have a poor outcome following transplant;

wherein the method comprises measuring the radiographic feature of nodule in the 6 lobes, wherein the radiograph lung score for nodule of greater than 2, greater than 3, greater than 4 or greater than 5 is indicative the donor lung is likely not suitable for transplant and/or the patient is likely to have a poor outcome following transplant; and/or wherein the method comprises measuring the radiographic feature of interstitial line in the 6 lobes, wherein the radiograph lung score for interstitial line of greater than 6, greater than 7, greater than 8 or greater than 9 is indicative the donor lung is likely not suitable for transplant and/or the patient is likely to have a poor outcome following transplant.

9. The method of claim 8, wherein the poor outcome following transplant is prolonged mechanical ventilation, optionally greater than three days, a graft-related death causes within 30 days, PGD3, extracorporeal life support, extracorporeal membrane oxygenation and/or prolonged hospital/ICU stays; and/or wherein the donor lung predicted as not likely suitable for transplant is declined for transplant or subject to perfusion or to further perfusion and optionally an assessment of radiographic features in a radiograph obtained at a later time point including 1 hour, 2 hours or 3 hours following initial assessment.

10. The method of claim 1, wherein the ex vivo lung is an ex vivo lung undergoing ex vivo lung perfusion (EVLP) and the radiograph is of a lung obtained during EVLP and the donor lung is in the EVLP machine, optionally the radiograph being obtained after about 15 minutes of EVLP, after about 30 minutes of EVLP, after about 1 hour of EVLP, after about 2 hours of EVLP, after about 3 hours of EVLP or after about 4 hours of EVLP.

11. A computer implemented method for predicting transplant suitability of an ex vivo donor lung and/or patient outcome following transplant of the donor lung, wherein the method is performed by at least one processor and the method comprises:

obtaining measurements of at least one or at least two radiographic feature(s) in a plurality of lobes of the donor lung from a radiograph of the donor lung, the radiographic features optionally selected from consolidation, infiltrate, atelectasis, nodule and interstitial line, and the plurality of lobes selected from right upper lobe, right middle lobe, right lower lobe, left upper lobe, lingula and left lower lobe;

determining in each of the lobes of the plurality of lobes a lobar score for each of the radiographic features measured;

combining the lobar score of each of the lobes of the plurality of lobes to generate a radiograph lung score for each of the radiographic features measured; and predicting the transplant suitability of the donor lung and/or patient outcome following transplant of the donor lung by providing the radiograph lung score for each of the radiographic features measured to a prediction model.

12. The computer-implemented method of claim 11, wherein the ex vivo donor lung is an ex vivo donor lung undergoing EVLP.

13. The computer-implemented method of claim 11, wherein the prediction model is an RLS model that compares the RLS to a control radiograph lung score or cut-off level for each radiographic feature to predict transplant suitability of a donor lung undergoing ex vivo lung perfusion and/or patient outcome following transplant of the donor lung.

14. The computer-implemented method of claim 11, wherein the prediction model is a univariate regression model that is determined for the radiographic features measured, the prediction model is a multivariate regression model that is determined for two or more of the radiographic features measured, or the prediction model is a multivariate regression model that is determined for one or more physiological measurements of the donor lung and for two or more of the radiographic features measured.

15. The computer-implemented method of claim 14, wherein the physiological measurements include oxygenation and/or edema.

16. The computer-implemented method of claim 11, wherein the prediction model is a machine learning model including a decision tree, or a neural network.

17. The computer-implemented method of claim 11, wherein AI-guided image analysis is performed on one or more x-ray images of the donor lung in the EVLP to determine one or more image-based features that are provided as input into the prediction model.

18. The computer-implemented method of claim 11, wherein the predicted transplant suitability of a donor lung undergoing ex vivo lung perfusion is classified as transplanted versus declined donor lungs, and/or wherein the predicted patient outcome following transplant of the donor lung is classified as based on various recipient mechanical ventilation outcomes.

19. The computer-implemented method of claim 11, wherein the radiograph obtained is of a lung after about 15 minutes of EVLP, after about 30 minutes of EVLP, after about 1 hour of EVLP, after about 2 hours of EVLP, after about 3 hours of EVLP or after about 4 hours of EVLP; or wherein the radiograph obtained is of a lung during EVLP and the donor lung is in the EVLP machine, optionally after about 15 minutes of EVLP, after about 30 minutes of EVLP, after about 1 hour of EVLP, after about 2 hours of EVLP, after about 3 hours of EVLP or after about 4 hours of EVLP.

20. A computer implemented method for predicting transplant suitability of an ex vivo donor lung and/or patient outcome following transplant of the donor lung, wherein the method is performed by at least one processor and the method comprises:

generating a prediction of a transplant suitability of the donor lung and/or patient outcome following transplant of the donor lung based on analyzing at least one radiograph of the donor lung using a machine learning model, wherein the machine learning model is trained on radiograph images.

21. The method of claim 20, wherein the model is trained on radiograph images labeled with scores for at least two radiographic features comprising consolidation, infiltrate, atelectasis, nodule and interstitial line.

22. The method of claim 20, wherein at least some of the labeled radiograph training images are labeled with an assessment of transplant suitability of the donor lung and/or patient outcome following transplant or the training images are labeled with scores associated with a relative degree of the at least two radiographic features in the training images.

23. The method of claim 20, wherein the machine learning model generates at least one score associated with a relative degree of the at least two radiographic features present in the at least one radiograph of the donor lung and the prediction is generated based on the at least one score.

24. The method of claim 20, wherein the prediction is generated based on providing, in addition to at least two radiograph features, at least one physiological, biochemical, donor, recipient and/or biological as inputs to the machine learning model.

* * * * *